(12) United States Patent
Watson et al.

(10) Patent No.: US 11,911,407 B2
(45) Date of Patent: Feb. 27, 2024

(54) THERAPIES FOR CARDIOMYOPATHY

(71) Applicant: UNIVERSITY COLLEGE DUBLIN, NATIONAL UNIVERSITY OF IRELAND, Dublin (IE)

(72) Inventors: Chris Watson, Dublin (IE); John Baugh, Dublin (IE); Mark Ledwidge, Cork (IE); Ken McDonald, Dublin (IE)

(73) Assignee: UNIVERSITY COLLEGE DUBLIN, NATIONAL UNIVERSITY OF IRELAND, Dublin (IE)

( * ) Notice: Subject to any disclaimer, the term of this patent is extended or adjusted under 35 U.S.C. 154(b) by 0 days.

(21) Appl. No.: 15/955,628

(22) Filed: Apr. 17, 2018

(65) Prior Publication Data
US 2019/0091253 A1 Mar. 28, 2019

Related U.S. Application Data

(62) Division of application No. 14/893,920, filed as application No. PCT/EP2014/060853 on May 26, 2014, now abandoned.

(30) Foreign Application Priority Data

May 25, 2013 (GB) ..................................... 1309444

(51) Int. Cl.
| | | |
|---|---|---|
| A61K 31/7064 | (2006.01) | |
| A61K 31/706 | (2006.01) | |
| A61K 31/713 | (2006.01) | |
| C12Q 1/6883 | (2018.01) | |
| G01N 33/50 | (2006.01) | |

(52) U.S. Cl.
CPC ........ *A61K 31/7064* (2013.01); *A61K 31/706* (2013.01); *A61K 31/713* (2013.01); *C12Q 1/6883* (2013.01); *G01N 33/5023* (2013.01); *C12Q 2600/136* (2013.01); *C12Q 2600/154* (2013.01); *C12Q 2600/158* (2013.01); *G01N 2500/02* (2013.01); *G01N 2500/04* (2013.01); *G01N 2500/10* (2013.01); *G01N 2800/325* (2013.01)

(58) Field of Classification Search
CPC .............. A61K 31/7064; C12Q 1/6883; C12Q 2600/136; C12Q 2600/158; C12Q 2600/154; G01N 33/5023; G01N 2500/10; G01N 2500/04; G01N 2500/02; G01N 2800/325
USPC .......................................................... 514/43
See application file for complete search history.

(56) References Cited

U.S. PATENT DOCUMENTS

| | | |
|---|---|---|
| 2009/0105168 A1 | 4/2009 | Gruber et al. |
| 2011/0319466 A1 | 12/2011 | Brooks et al. |
| 2012/0014962 A1 | 1/2012 | Mann et al. |

FOREIGN PATENT DOCUMENTS

| | | | |
|---|---|---|---|
| WO | WO-2004/072261 A2 | 8/2004 | |
| WO | WO-2006/121532 A2 | 11/2006 | |
| WO | WO-2014191364 A1 * | 12/2014 | ........... A61K 31/706 |

OTHER PUBLICATIONS

Haas et al. (EMBO Mol Med. Mar. 2013; 5(3):413-29).*
Fahy et al. (Expert Opin. Ther. Patents (2012) 22(12), 1427-1442).*
Matoušová et al. (Epigenetics 6:6, 769-776; Jun. 2011).*
Montesano et al. (International Journal of Biological Sciences, 2013; 9(4):391-402).*
Marian et al. (J Mol Cell Cardiol. Apr. 2001 ; 33(4): 655-670).*
Deng et al. (Journal of Geriatric Cardiology Sep. 2009, vol. 6, No. 3, 182-188).*
Harvey et al. (J. Cell Biol. vol. 194 No. 3 355-365).*
CDC, Heart Disease, Cardiomyopathy, internet article, Feb. 21, 2023. (Year: 2023).*
Steensma, J Clin Oncol 27:3842-3848, 2009. (Year: 2009).*
Bacanamwo M et al. (2007), "Abstract 668: Inhibition of DNA Methyltransferase Inhibits the Ang II-Induced Increase in Blood Pressure, Vascular Remodeling and Target Organ Damage", Circulation (2007), 116:11, 124 (Abstract).
Baccarelli, Andrea et al., "Ischemic heart disease and stroke in relation to blood DNA methylation," Epidemiology, (2010), vol. 21, No. 6, pp. 819-828.
Bekeredjian, Raffi et al., "Conditional HIF-1α Expression Produces a Reversible Cardiomyopathy," Plosone, (2010), vol. 5, No. 7, pp. E11693, (12 total pages).
Cirino A Al et al. (2014), "Hypertrophic Cardiomyopathy Overview", GeneReviews [Internet], Online Review, Initial Posting: Aug. 5, 2008; Last Updated: Jan. 16, 2014, downloaded from http://www.ncbi.nlm.nih.gov/books/NBK1768/ on May 5, 2016.
Esha et al. (2002), "Pharmacologic myocardial regeneration using 5-Aza-2'deoxycytidine", FASEB Journal, vol. 16, p. A491.
Haas, Jan et al., "Alterations in Cardiac DNA Methylation in Human Dilated Cardiomyopathy," EMBO Mol Med, (2013), vol. 5, No. 3, pp. 413-429.
International Search Report and Written Opinion of the International Searching Authority received for Application No. PCT/EP2014/060853 dated Apr. 8, 2014, 9 pages total.
Kao, Yu-Hsun et al., "Hydralazine-induced promoter demethylation enhances sarcoplasmic reticulum Ca2+-ATPase and calcium homeostasis in cardiac myocytes," Laboratory Investigation, (2011), vol. 91, pp. 1291-1297.
Merkulov S et al. (2012), "In Vivo Cardiac Myosin Binding Protein C Gene Transfer Rescues Myofilament Contractile Dysfunction in Cardiac Myosin Binding Protein C Null Mice", Circ Heart Fail. 2012, 5:635-644.
Meurs, Kathryn M. et al., "Differential Methylation of CpG Sites in Two Isoforms of Myosin Binding Protein C, an Important Hypertrophic Cardiomyopathy Gene," Environ Mol Mutagen, (2011), vol. 52, No. 2, pp. 161-164.

(Continued)

Primary Examiner — Layla D Berry
(74) Attorney, Agent, or Firm — Foley & Lardner LLP

(57) ABSTRACT

The present invention relates to therapies and therapeutic agents for use in the treatment of cardiomyopathies. In particular, the invention is concerned with, but not limited to therapies and therapeutic agents for use in the treatment of hypertrophic cardiomyopathy. Such therapeutic agents comprise hypomethylating agents.

16 Claims, 13 Drawing Sheets

Specification includes a Sequence Listing.

(56) References Cited

OTHER PUBLICATIONS

Movassagh, Mehregan et al., Differential DNA Methylation Correlates with Differential Expression of Angiogenic Factors in Human Heart Failure, PLOS One, (2010), vol. 5, No. 1, pp. e8564 (7 total pages).

Page, Stephen P. et al., "Cardiac Myosin Binding Protein-C Mutations in Families with Hypertrophic Cardiomyopathy," Circ. Cardio. Genetics, (2012), vol. 5, pp. 156-166.

Stresemann, et al., "Modes of action of the DNA methyltransferase inhibitors azacytidine and decitabine", Int. J. Cancer: 123, 8-13 (2008).

Taylor, Anne L. et al., "Combination of Isosorbide Dinitrate and Hydralazine in Blacks with Heart Failure," New England Journal of Medicine, (2004), vol. 251, No. 20, pp. 2049-2057.

U.S. Office Action dated Oct. 19, 2017, from U.S. Appl. No. 14/893,920.

Moore et al., "DNA Methylation and Its Basic Function", Neuropsychopharmacology, 2013, 38, pp. 23-38.

* cited by examiner

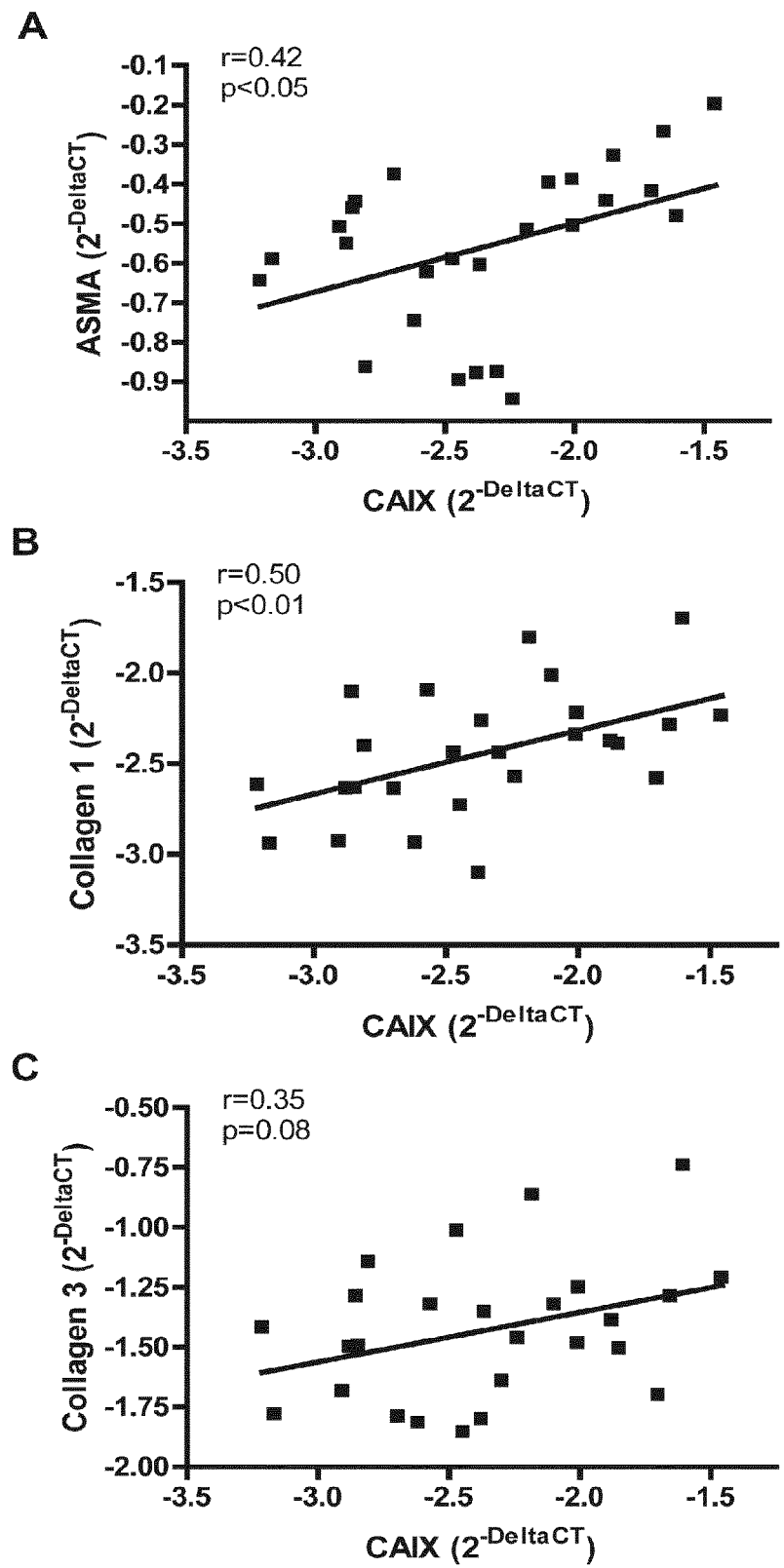
Figure 1a-c

D
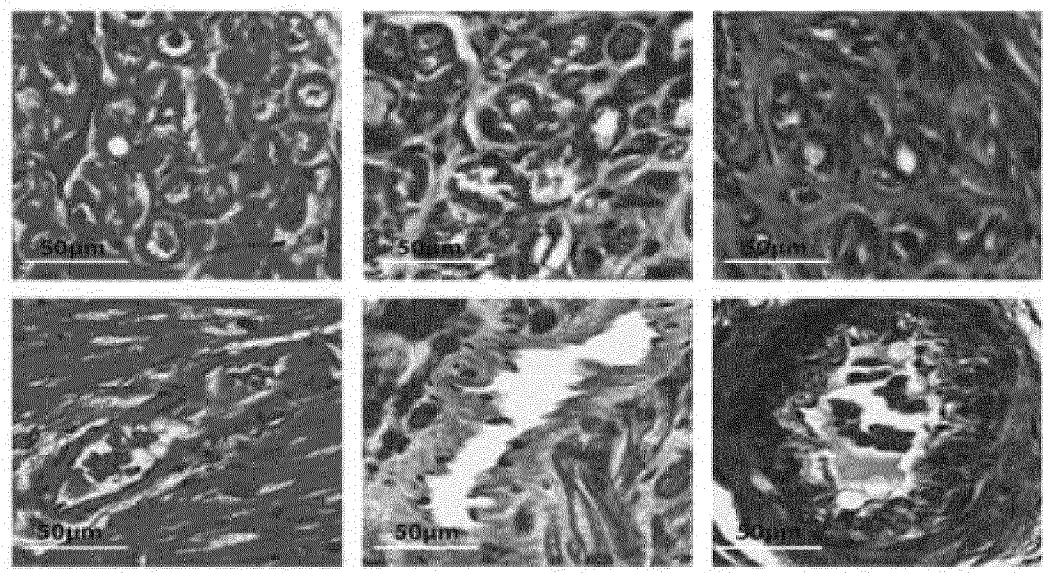
E
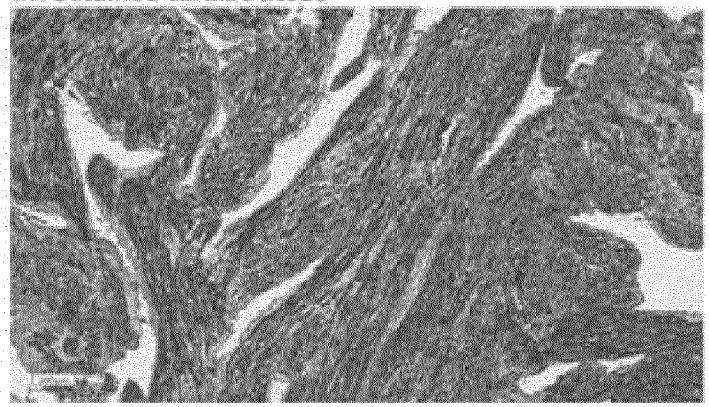
MTC stained cardiac tissue
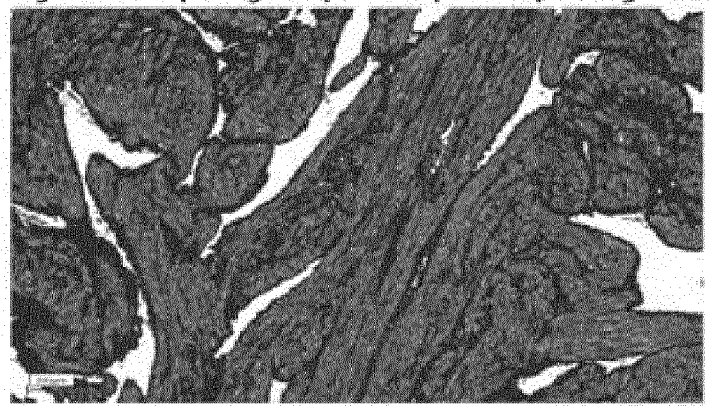
Digital mark-up image output from positive pixel algorithm
Figure 1 d-e

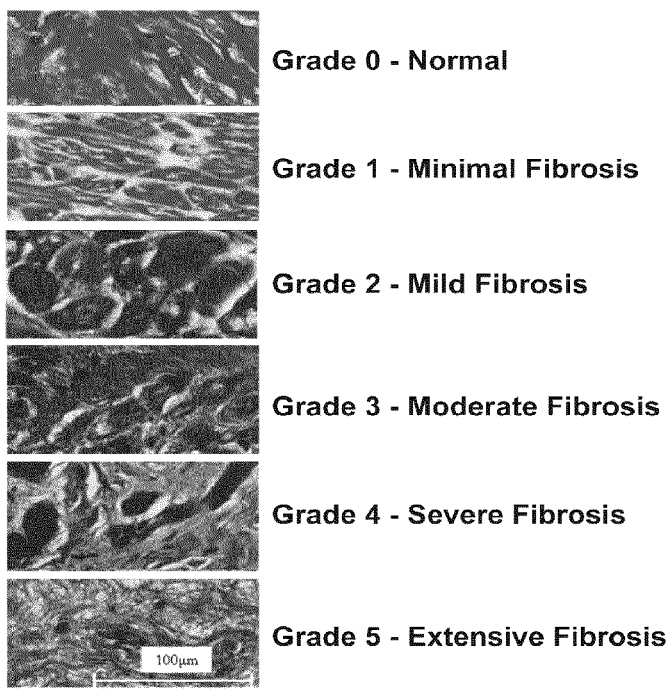
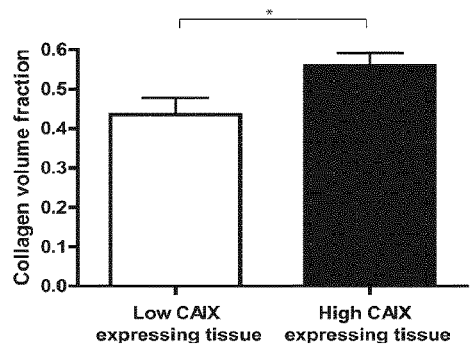
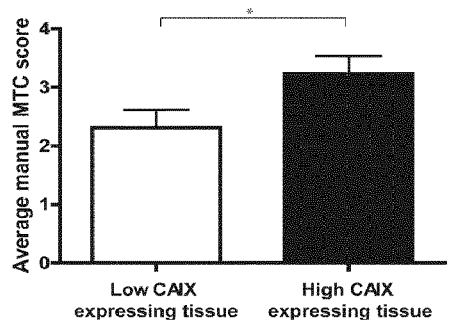
Figure 1 f-h

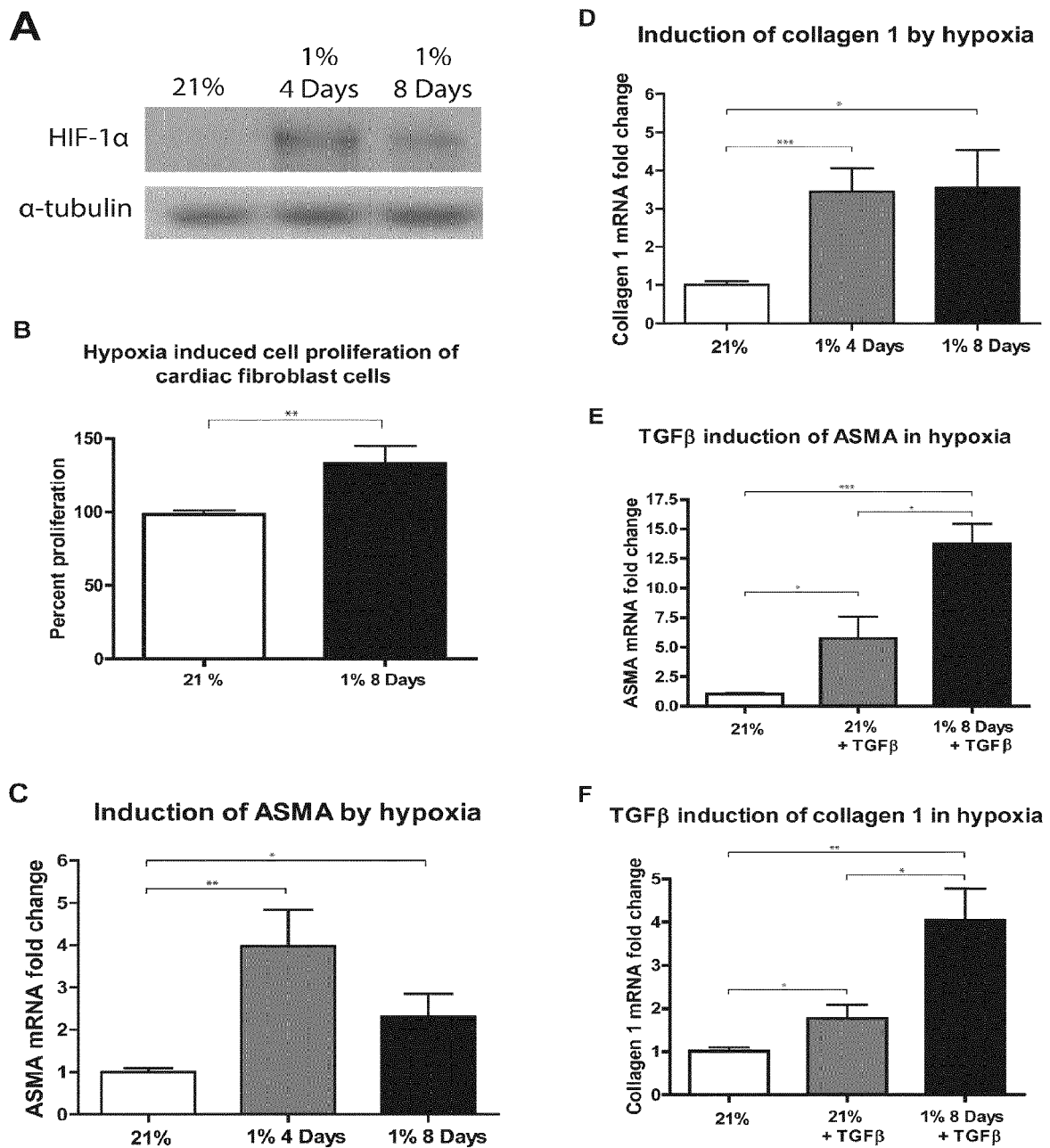
Figure 2a-f

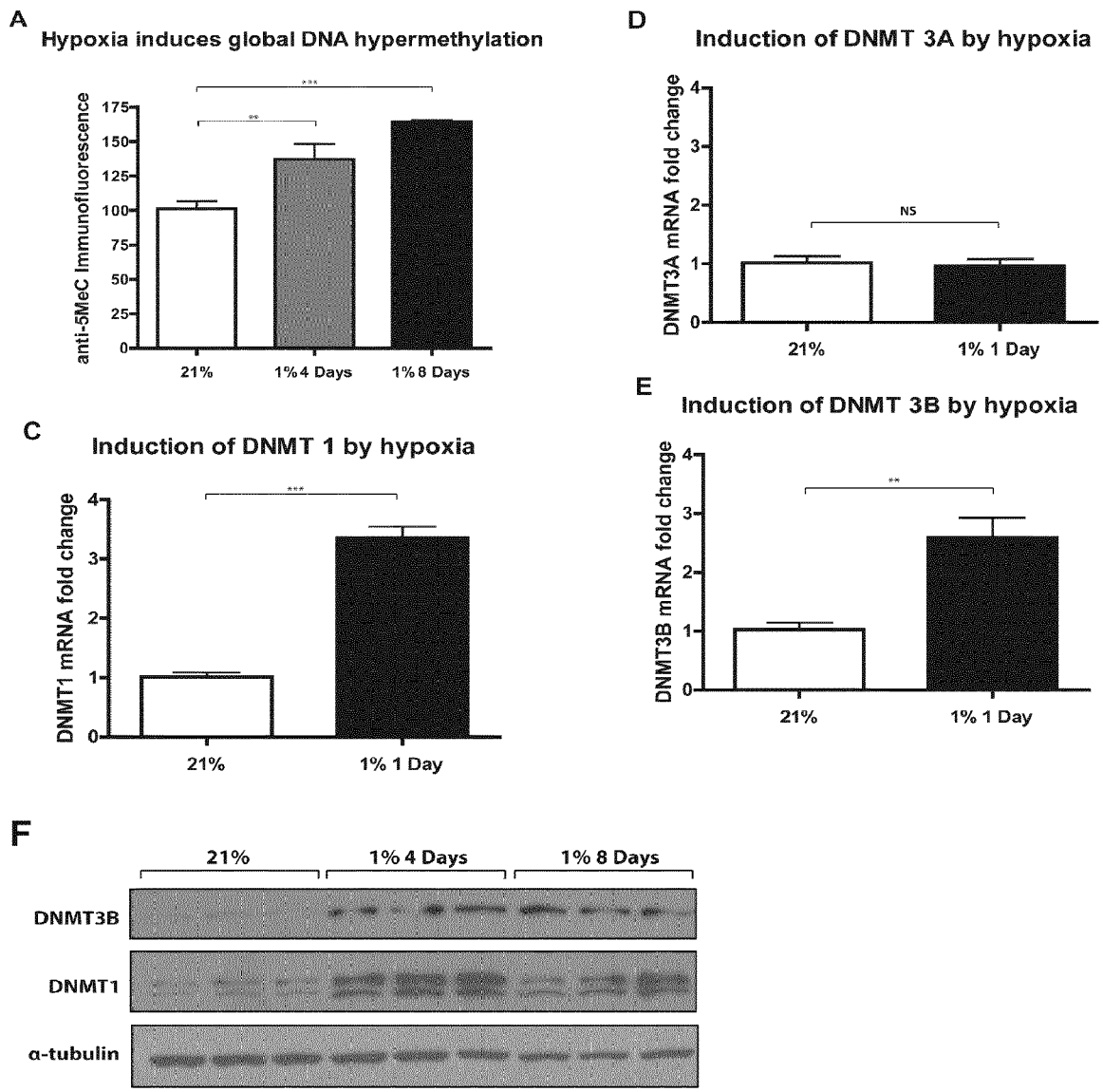
Figures 3a, 3c-f

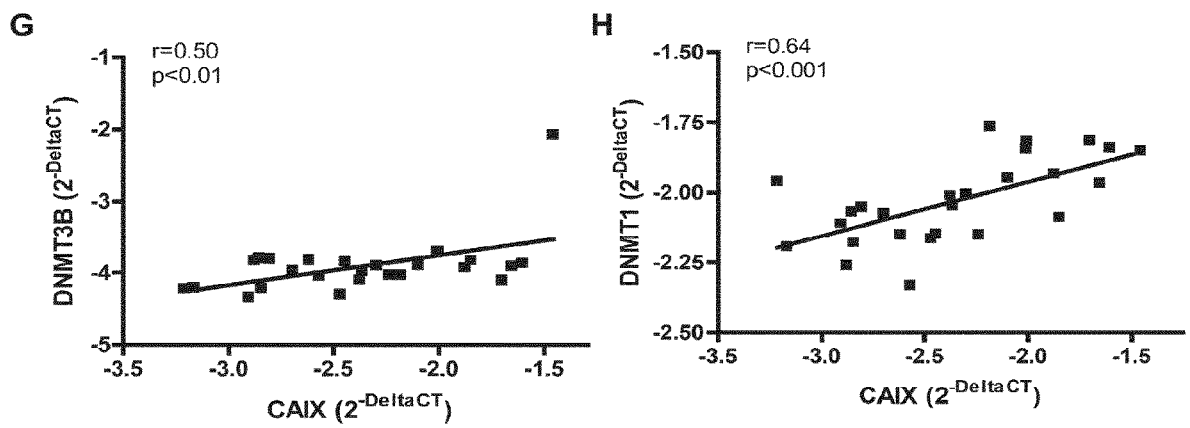
Figure 3g, 3h
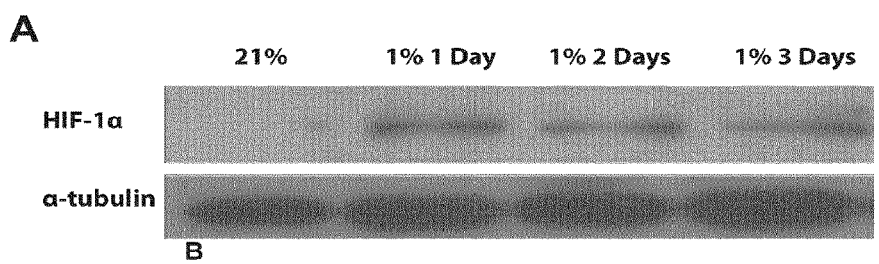
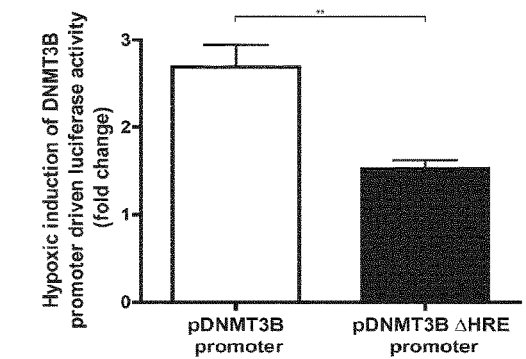
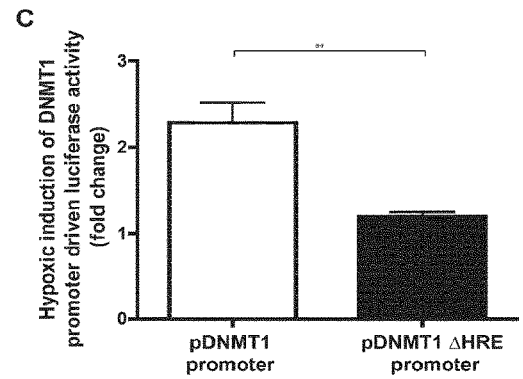
Figure 4 a-c

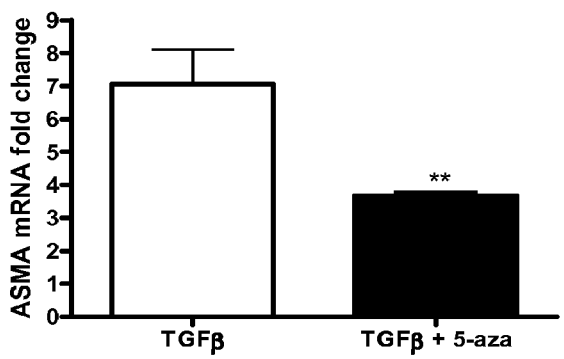
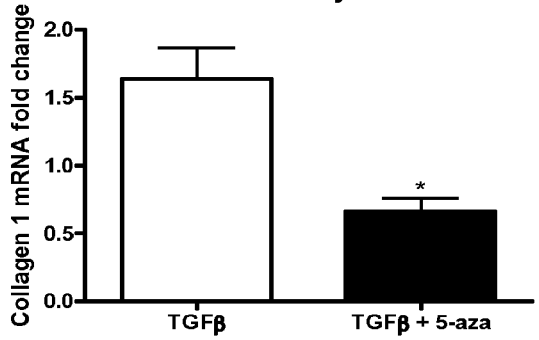
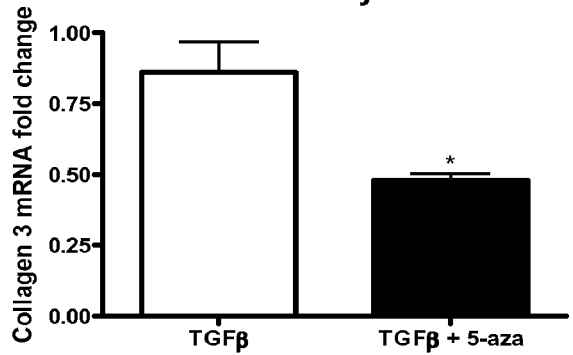
Figure 7a-c

DNMT1 Promoter Wild-Type

GAGATGCAGTTTCTCTATGTTACCtaggctggtctaaaactcctgggctcaagcgatcctcccaccctggcctcccaa
agtgctgggatgacaggcGTGAGCCACGTGGTGCTtaaaaaaggcaacaaaaaacccccacacactgggtataga
agtggcatgggcctctatacactgtgagattcttggtactagctacaaattctgtgtatactcaagattttctagagtaggtgcaattacccc
gttttacagatgaggacacagaggctgagccgtagtgacccacctaaggtcgtatagccagcaaatagatggaggttggattggaac
tgaggactttactcaagggctctcacaaaccttgggggcttctcgctgctttatccccatcacacctgaaagaatgaatgaatgaatgc
ctcgggcaccgtgcccacctcccagcaaaccgtggagcttggacgagcccactgctccgcgtggggggggtgtgtgcccgccttgc
gcatgcgtgttccctgggcatggccggctccgttccatccttctgcacagggtatcgcctctctccgtttggtacatcccctcctcccccac
gcccggactggggtggtagacgccgcctccgctcatcgcccctcccatcggtttccgcgcgaaaagccggggcgcctgcgctgcc
gccgccgcgtcTGCTGAAGCCTCCGAGATgccggcgc

| Forward Primer with XhoI | CTCGAGGAGATGCAGTTTCTCTATGTTACC |
|---|---|
| Reverse Primer with HindIII | AAGCTTATCTCGGAGGCTTCAGCA |

Green = Forward Primer without XhoI
Cyan = Reverse Primer without HindIII (sequence is reversed and complemented to primer)
Red Text = Hypoxia response element (HRE)
Yellow & Bold = Site-Directed Mutagenesis/Bases Changed

Figure 23

DNMT1 Mutant Site V$HIFF (97-113)

GAGATGCAGTTTCTCTATGTTACCtaggctggtctaaaactcctgggctcaagcgatcctcccaccctggcctcccaa
agtgctgggatgacaggcGTGAGCCTAGTGGTGCTtaaaaaaggcaacaaaaaacccccacacactgggtataga
agtggcatgggcctctatacactgtgagattcttggtactagctacaaattctgtgtatactcaagattttctagagtaggtgcaattacccc
gttttacagatgaggacacagaggctgagccgtagtgacccacctaaggtcgtatagccagcaaatagatggaggttggattggaac
tgaggactttactcaagggctctcacaaaccttgggggcttctcgctgctttatccccatcacacctgaaagaatgaatgaatgaatgc
ctcgggcaccgtgcccacctcccagcaaaccgtggagcttggacgagcccactgctccgcgtggggggggtgtgtgcccgccttgc
gcatgcgtgttccctgggcatggccggctccgttccatccttctgcacagggtatcgcctctctccgtttggtacatcccctcctcccccac
gcccggactggggtggtagacgccgcctccgctcatcgcccctcccatcggtttccgcgcgaaaagccggggcgcctgcgctgcc
gccgccgcgtcTGCTGAAGCCTCCGAGATgccggcgc Mutant Primers (Designed with Primer X)

| Forward Primer | 5' GGATGACAGGCGTGAGCCTAGTGGTGCTTAAAAAAGGC 3' |
|---|---|
| Reverse Primer | 5' GCCTTTTTTAAGCACCACTAGGCTCACGCCTGTCATCC 3' |

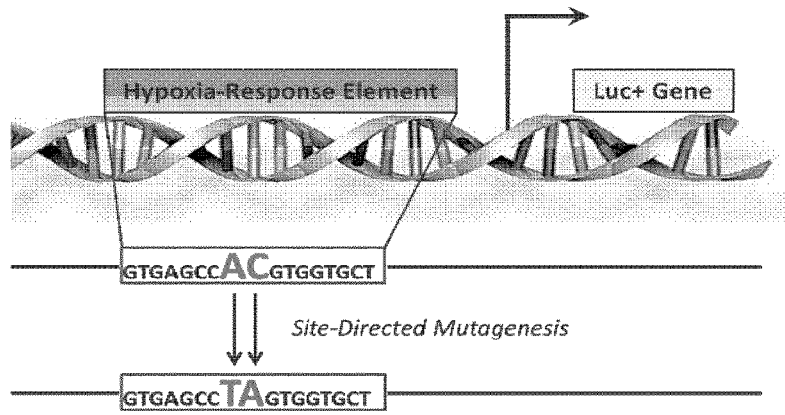

Figure 24

DNMT3b Promoter Wild-Type

GGGCCGGGGCTACAAGGGGAGTCGGCACCGCCCCCTCCCCacccactcccgctgccccgtccggccc
gcgccgcttcctcgcagcagctgctcccggctccgcggccGCAGCCCGCGTGGACGCtccgagcgccccccgacgga
cgggaccggctccctggcggtCgggcgagcgggcggcaacgctgcccggccggcagcgctggggttaagtggcccaagTAAA
CCTAGCTCGGCGATCGGCGC

| Forward Primer with XhoI | CTCGAGGGGCCGGGGCTACAAGGGGAGT |
| Reverse Primer with HindIII | AAGCTTGCGCCGATCGCCGAGCTAGGTTTA |

Green = Forward Primer without XhoI
Cyan = Reverse Primer without HindIII (sequence is reversed and complemented to primer)
Red Text = HRE
Yellow & Bold = Site-Directed Mutagenesis/Bases Changed

Figure 25

DNMT3b Mutant Site V$HIFF (108-124)

GGGCCGGGGCTACAAGGGGAGTCGGCACCGCCCCCTCCCCacccactcccgctgccccgtccggccc
gcgccgcttcctcgcagcagctgctcccggctccgcggccGCAGACCGAGTGGACGCtccgagcgccccccgacgga
cgggaccggctccctggcggtCgggcgagcgggcggcaacgctgcccggccggcagcgctggggttaagtggcccaagTAAA
CCTAGCTCGGCGATCGGCGC Mutant Primers (Designed with Primer X)

| Forward Primer | 5' GCTCCGCGGCCGCAGACCGAGTGGACGCTCCGAGC 3' |
| Reverse Primer | 5' GCTCGGAGCGTCCACTCGGTCTGCGGCCGCGGAGC 3' |

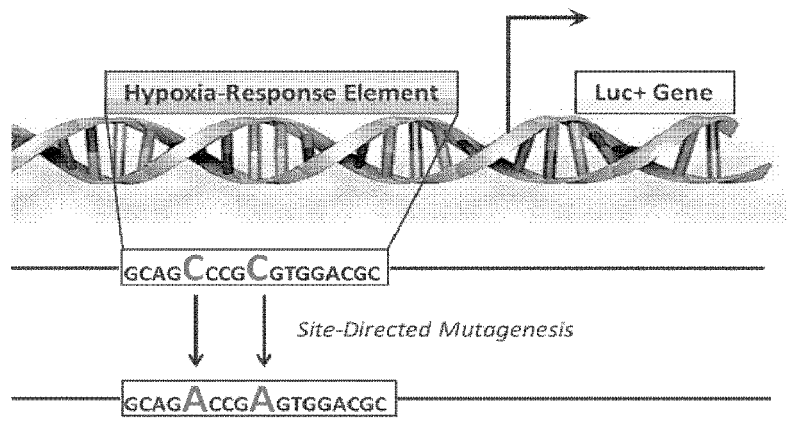

Figure 26

SEQUENCE LISTING

```
<160> NUMBER OF SEQ ID NOS: 31

<210> SEQ ID NO 1
<211> LENGTH: 725
<212> TYPE: DNA
<213> ORGANISM: Homo sapiens
<220> FEATURE:
<221> NAME/KEY: source
<222> LOCATION: 1..725
<223> OTHER INFORMATION: /mol_type="unassigned DNA"
      /organism="Homo sapiens"
<220> FEATURE:
<221> NAME/KEY: primer_bind
<222> LOCATION: 1..24
<223> OTHER INFORMATION: /note="Forward Primer without XhoI"
<220> FEATURE:
```

```
<221> NAME/KEY: protein_bind
<222> LOCATION: 97..113
<223> OTHER INFORMATION: /function="Hypoxia response element (HRE)"
<220> FEATURE:
<221> NAME/KEY: primer_bind
<222> LOCATION: 700..717
<223> OTHER INFORMATION: /note="Reverse Primer without HindIII (sequence
      is reversed and complemented to primer)"

<400> SEQUENCE: 1
gagatgcagt ttctctatgt tacctaggct ggtctaaaac tcctgggctc aagcgatcct      60
cccaccctgg cctcccaaag tgctgggatg acaggcgtga gccacgtggt gcttaaaaaa     120
ggcaacaaaa aaccccccac acactgggta tagaagtggc atgggcctct atacactgtg     180
agattcttgg tactagctac aaattctgtg tatactcaag attttctaga gtaggtgcaa     240
ttaccccgtt ttacagatga ggacacagag gctgagccgt agtgacccac ctaaggtcgt     300
atagccagca aatagatgga ggttggattg gaactgagga ctttactcaa gggctctcac     360
aaacccttgg gggcttctcg ctgctttatc cccatcacac ctgaaagaat gaatgaatga     420
atgcctcggg caccgtgccc acctcccagc aaaccgtgga gcttggacga gcccactgct     480
ccgcgtgggg ggggtgtgtg cccgccttgc gcatggcgtgt tccctgggca tggccggctc     540
cgttccatcc ttctgcacag ggtatcgcct ctctccgttt ggtacatccc ctcctccccc     600
acgcccggac tggggtggta gacgccgcct ccgctcatcg cccctcccca tcggtttccg     660
cgcgaaaagc cggggcgcct gcgctgccgc cgccgcgtct gctgaagcct ccgagatgcc     720
ggcgc                                                                 725

<210> SEQ ID NO 2
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="unassigned DNA"
      /note="Forward Primer with XhoI"
      /organism="Artificial Sequence"
<220> FEATURE:
<221> NAME/KEY: misc_feature
<222> LOCATION: 1..6
<223> OTHER INFORMATION: /function="XhoI restriction site"

<400> SEQUENCE: 2
ctcgaggaga tgcagtttct ctatgttacc                                      30

<210> SEQ ID NO 3
<211> LENGTH: 24
<212> TYPE: DNA
<213> ORGANISM: Artificial Sequence
<220> FEATURE:
<221> NAME/KEY: source
<222> LOCATION: 1..24
<223> OTHER INFORMATION: /mol_type="unassigned DNA"
      /note="DNAMT1 reverse primer with Hind iii"
      /organism="Artificial Sequence"
<220> FEATURE:
<221> NAME/KEY: misc_feature
<222> LOCATION: 1..6
<223> OTHER INFORMATION: /function="HindIII restriction site"

<400> SEQUENCE: 3
aagcttatct cggaggcttc agca                                            24

<210> SEQ ID NO 4
```

```
<211> LENGTH: 725
<212> TYPE: DNA
<213> ORGANISM: Artificial Sequence
<220> FEATURE:
<221> NAME/KEY: source
<222> LOCATION: 1..725
<223> OTHER INFORMATION: /mol_type="unassigned DNA"
      /note="DNMT1 Mutant Site V$HIFF (97-113)"
      /organism="Artificial Sequence"
<220> FEATURE:
<221> NAME/KEY: primer_bind
<222> LOCATION: 1..24
<223> OTHER INFORMATION: /note="Forward Primer without XhoI"
<220> FEATURE:
<221> NAME/KEY: protein_bind
<222> LOCATION: 97..113
<223> OTHER INFORMATION: /function="Hypoxia response element (HRE) (HIF
      binding site)"
<220> FEATURE:
<221> NAME/KEY: variation
<222> LOCATION: 104..105
<223> OTHER INFORMATION: /note="Site-Directed Mutagenesis/Bases Changed"
<220> FEATURE:
<221> NAME/KEY: primer_bind
<222> LOCATION: 700..717
<223> OTHER INFORMATION: /note="Reverse Primer without HindIII (sequence
      is reversed and complemented to primer)"

<400> SEQUENCE: 4
gagatgcagt ttctctatgt tacctaggct ggtctaaaac tcctgggctc aagcgatcct    60
cccaccctgg cctcccaaag tgctgggatg acaggcgtga gccagtggt gcttaaaaaa   120 ggcaacaaaa aaccccccac acactgggta tagaagtggc atgggcctct atacactgtg   180
agattcttgg tactagctac aaattctgtg tatactcaag attttctaga gtaggtgcaa   240
ttaccccgtt ttacagatga ggacacagag gctgagccgt agtgacccac ctaaggtcgt   300
atagccagca aatagatgga ggttggattg gaactgagga ctttactcaa gggctctcac   360
aaaaccttgg gggcttctcg ctgctttatc cccatcacac ctgaaagaat gaatgaatga   420
atgcctcggg caccgtgccc acctcccagc aaaccgtgga gcttggacga gcccactgct   480
ccgcgtgggg ggggtgtgtg cccgccttgc gcatgcgtgt tccctgggca tggccggctc   540
cgttccatcc ttctgcacag ggtatcgcct ctctccgttt ggtacatccc ctcctccccc   600
acgcccggac tggggtggta gacgccgcct ccgctcatcg cccctcccca tcggtttccg   660
cgcgaaaagc cggggcgcct gcgctgccgc cgccgcgtct gctgaagcct ccgagatgcc   720
ggcgc                                                              725

<210> SEQ ID NO 5
<211> LENGTH: 38
<212> TYPE: DNA
<213> ORGANISM: Artificial Sequence
<220> FEATURE:
<221> NAME/KEY: source
<222> LOCATION: 1..38
<223> OTHER INFORMATION: /mol_type="unassigned DNA"
      /note="Forward Primer"
      /organism="Artificial Sequence"

<400> SEQUENCE: 5
ggatgacagg cgtgagccta gtggtgctta aaaaaggc                           38

<210> SEQ ID NO 6
<211> LENGTH: 38
<212> TYPE: DNA
<213> ORGANISM: Artificial Sequence
<220> FEATURE:
<221> NAME/KEY: source
```

<222> LOCATION: 1..38
<223> OTHER INFORMATION: /mol_type="unassigned DNA"
      /note="DNMT1 Mutant Reverse Primer"
      /organism="Artificial Sequence"

<400> SEQUENCE: 6
gcctttttta agcaccacta ggctcacgcc tgtcatcc         38

<210> SEQ ID NO 7
<211> LENGTH: 246
<212> TYPE: DNA
<213> ORGANISM: Homo sapiens
<220> FEATURE:
<221> NAME/KEY: source
<222> LOCATION: 1..246
<223> OTHER INFORMATION: /mol_type="unassigned DNA"
      /note="DNMT3b Promoter Wild-Type"
      /organism="Homo sapiens"
<220> FEATURE:
<221> NAME/KEY: primer_bind
<222> LOCATION: 1..22
<223> OTHER INFORMATION: /note="Forward Primer without XhoI"
<220> FEATURE:
<221> NAME/KEY: protein_bind
<222> LOCATION: 108..124
<223> OTHER INFORMATION: /function="Hypoxia response element (HRE) (HIF
      binding site)"
<220> FEATURE:
<221> NAME/KEY: primer_bind
<222> LOCATION: 223..246
<223> OTHER INFORMATION: /note="Reverse Primer without HindIII (sequence
      is reversed and complemented to primer)"

<400> SEQUENCE: 7
gggccggggc tacaagggga gtcggcaccg cccccteccc acccactccc gctgccccgt   60
ccggcccgcg ccgcttcctc gcagcagctg ctcccggctc cgcggccgca gcccgcgtgg   120
acgctccgag cgcccccga cggacgggac cggctccctg gcggtcgggc gagcgggcgg   180
caacgctgcc cggccggcag cgctgggggtt aagtggccca agtaaaccta gctcggcgat   240
cggcgc                                                              246

<210> SEQ ID NO 8
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /mol_type="unassigned DNA"
      /note="DNMT3b Forward Primer with XhoI"
      /organism="Artificial Sequence"
<220> FEATURE:
<221> NAME/KEY: misc_feature
<222> LOCATION: 1..6
<223> OTHER INFORMATION: /function="XhoI restriction site"

<400> SEQUENCE: 8
ctcgaggggc cggggctaca agggagt                    28

<210> SEQ ID NO 9
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="unassigned DNA"
      /note="Reverse Primer with HindIII"
      /organism="Artificial Sequence"
<220> FEATURE:

```
<221> NAME/KEY: misc_feature
<222> LOCATION: 1..6
<223> OTHER INFORMATION: /function="HindIII restriction site"

<400> SEQUENCE: 9
aagcttgcgc cgatcgccga gctaggttta                                    30

<210> SEQ ID NO 10
<211> LENGTH: 246
<212> TYPE: DNA
<213> ORGANISM: Artificial Sequence
<220> FEATURE:
<221> NAME/KEY: source
<222> LOCATION: 1..246
<223> OTHER INFORMATION: /mol_type="unassigned DNA"
     /note="DNMT3b Mutant Site V$HIFF (108-124)"
     /organism="Artificial Sequence"
<220> FEATURE:
<221> NAME/KEY: primer_bind
<222> LOCATION: 223..246
<223> OTHER INFORMATION: /note="Reverse Primer without HindIII (sequence
     is reversed and complemented to primer)"
<220> FEATURE:
<221> NAME/KEY: primer_bind
<222> LOCATION: 1..22
<223> OTHER INFORMATION: /note="Forward Primer without XhoI"
<220> FEATURE:
<221> NAME/KEY: protein_bind
<222> LOCATION: 108..124
<223> OTHER INFORMATION: /function="Hypoxia response element (HRE) (HIF
     binding site)"
<220> FEATURE:
<221> NAME/KEY: variation
<222> LOCATION: 112,116
<223> OTHER INFORMATION: /note="Site-Directed Mutagenesis/Bases Changed"

<400> SEQUENCE: 10
gggccggggc tacaagggga gtcggcaccg cccctcccc acccactccc gctgccccgt      60
ccggcccgcg ccgcttcctc gcagcagctg ctccggctc gcggccgca gaccgagtgg     120 acgctccgag cgccccccga cggacgggac cggctccctg gcggtcgggc gagcgggcgg   180
caacgctgcc cggccggcag cgctgggggtt aagtggccca agtaaaccta gctcggcgat  240
cggcgc                                                              246

<210> SEQ ID NO 11
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="unassigned DNA"
     /note="DNAMT3b Mutant Forward Primer"
     /organism="Artificial Sequence"

<400> SEQUENCE: 11
gctccgcggc cgcagaccga gtggacgctc cgagc                              35

<210> SEQ ID NO 12
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="unassigned DNA"
     /note="DNAMT3b Mutant Reverse Primer"
     /organism="Artificial Sequence"

<400> SEQUENCE: 12
```
gctcggagcg tccactcggt ctgcggccgc ggagc                          35

<210> SEQ ID NO 13
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="unassigned DNA"
      /note="Alpha Smooth Muscle Actin Forward Primer"
      /organism="Artificial Sequence"

<400> SEQUENCE: 13
cgttactact gctgagcgtg a                                         21

<210> SEQ ID NO 14
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="Alpha smooth muscle actin"
      /organism="Artificial Sequence"

<400> SEQUENCE: 14
aacgttcatt tccgatggtg                                           20

<210> SEQ ID NO 15
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="Collagen 1 ?1 Forward Primer"
      /organism="Artificial Sequence"

<400> SEQUENCE: 15
gaacgcgtgt catcccttgt                                           20

<210> SEQ ID NO 16
<211> LENGTH: 24
<212> TYPE: DNA
<213> ORGANISM: Artificial Sequence
<220> FEATURE:
<221> NAME/KEY: source
<222> LOCATION: 1..24
<223> OTHER INFORMATION: /mol_type="unassigned DNA"
      /note="Collagen 1 ?1 Reverse Primer"
      /organism="Artificial Sequence"

<400> SEQUENCE: 16
gaacgaggta gtctttcagc aaca                                      24

<210> SEQ ID NO 17
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="unassigned DNA"
      /note="Collagen 3 ?1 Forward Primer"
      /organism="Artificial Sequence"

```
<400> SEQUENCE: 17
aacacgcaag gctgtgagac t                                            21

<210> SEQ ID NO 18
<211> LENGTH: 24
<212> TYPE: DNA
<213> ORGANISM: Artificial Sequence
<220> FEATURE:
<221> NAME/KEY: source
<222> LOCATION: 1..24
<223> OTHER INFORMATION: /mol_type="unassigned DNA"
      /note="Collagen 3 ?1 Reverse Primer"
      /organism="Artificial Sequence"

<400> SEQUENCE: 18
gaacgaggta gtctttcagc aaca                                         24

<210> SEQ ID NO 19
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="Carbonic anhydrase IX"
      /organism="Artificial Sequence"

<400> SEQUENCE: 19
aggtcccagg actggacata                                              20

<210> SEQ ID NO 20
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="Carbonic anhydrase IX Reverse Primer"
      /organism="Artificial Sequence"

<400> SEQUENCE: 20
gagggtgtgg agctgcttag                                              20

<210> SEQ ID NO 21
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="DNA methyltransferase 1 Forward Primer"
      /organism="Artificial Sequence"

<400> SEQUENCE: 21
tatccgagga gggctacctg                                              20

<210> SEQ ID NO 22
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="DNA methyltransferase 1 Reverse Primer"
      /organism="Artificial Sequence"
```

```
<400> SEQUENCE: 22
cacttcccgg ttgtaagcat                                          20

<210> SEQ ID NO 23
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="DNA methyltransferase 3A"
      /organism="Artificial Sequence"

<400> SEQUENCE: 23
agcccaaggt caaggagatt                                          20

<210> SEQ ID NO 24
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="DNA methyltransferase 3A Reverse Primer"
      /organism="Artificial Sequence"

<400> SEQUENCE: 24
gttcttgcag ttttggcaca                                          20

<210> SEQ ID NO 25
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="DNA methyltransferase 3B Forward Primer"
      /organism="Artificial Sequence"

<400> SEQUENCE: 25
tcaggatggg aaggagtttg                                          20

<210> SEQ ID NO 26
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="DNA methyltransferase 3B Reverse Primer"
      /organism="Artificial Sequence"

<400> SEQUENCE: 26
ctgcagagac ctcggagaac                                          20

<210> SEQ ID NO 27
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="Beta-2-microglobulin Forward Primer"
```

```
        /organism="Artificial Sequence"

<400> SEQUENCE: 27
aggctatcca gcgtactcca                                                    20

<210> SEQ ID NO 28
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="Beta-2-microglobulin Reverse Primer"
      /organism="Artificial Sequence"

<400> SEQUENCE: 28
ccagtccttg ctgaaagaca                                                    20

<210> SEQ ID NO 29
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="Myosin binding protein C Forward Primer"
      /organism="Artificial Sequence"

<400> SEQUENCE: 29
ctggagacct ggacctcaga                                                    20

<210> SEQ ID NO 30
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="Myosin binding protein C Reverse Primer"
      /organism="Artificial Sequence"

<400> SEQUENCE: 30
ccggaaactg ctcttcttca                                                    20

<210> SEQ ID NO 31
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="other RNA"
      /note="DNMT3B siRNA"
      /organism="Artificial Sequence"

<400> SEQUENCE: 31
agaugacgga ugccuagagu u                                                  21
```

THERAPIES FOR CARDIOMYOPATHY

FIELD OF THE INVENTION

The present invention relates to therapies and therapeutic agents for use in the treatment of cardiomyopathies. In particular, the invention is concerned with, but not limited to therapies and therapeutic agents for use in the treatment of hypertrophic cardiomyopathy.

BACKGROUND TO THE INVENTION

The strict definition of cardiomyopathy is a myocardial disorder in which heart muscle is structurally and functionally abnormal. The vast majority of cardiomyopathy is extrinsic (external causes) and of these, the ischemic form is the most common. The term "ischemic cardiomyopathy" typically refers to remodeled and hypertrophied myocardium as a result of inadequate oxygen delivery to the myocardium, with coronary artery disease being the most common cause. Ischemic cardiomyopathy may therefore be regarded as a first subtype of cardiomyopathy.

The term "cardiomyopathy" is also sometimes used to specifically describe non-ischemic forms of cardiomyopathy, often with intrinsic/idiopathic causes. These non-ischemic cardiomyopathies may therefore be regarded as a second subtype of cardiomyopathy. Even though these diseases may be classified as non-ischemic, a relative myocardial hypoxia may nevertheless occur with such diseases. The classification of these forms is often on a functional/structural basis. Many of the forms of non-ischemic cardiomyopathy are associated with abnormalities of the genes encoding sarcomeric proteins, the commonest types of which are hypertrophic cardiomyopathy and dilated cardiomyopathy, and combinations of myocardial hypertrophy and/or fibrosis occur in these diseases. Other types of non-ischemic cardiomyopathy include restrictive cardiomyopathy, arrhythmogenic right ventricular cardiomyopathy and endomyocardial fibrosis. A brief summary of these diseases is as follows.

Hypertrophic cardiomyopathy (HCM) is often inherited and is discussed in more detail below. Patients present with dyspnoea due to diastolic dysfunction, chest pain, impaired diastole of hypertrophied myocardium, arrhythmias and presyncope/syncope due to inadequate cardiac output. HCM is characterised by disorganised cardiac myocytes and unexplained left ventricular hypertrophy, often due to mutations in the genes encoding sarcomeric proteins, such as cardiac beta-myosin heavy chain gene, myosin binding protein C3, troponin and alpha-tropomyosin. HCM patients undergo risk stratification using regular exercise testing and Holter monitoring, family screening and drug therapy, often with avoidance of physical exertion. Indicators of a high risk for poor outcome such as sudden cardia death include diagnosis at age <30 years, unexplained syncope, family history of early sudden cardiac death, cardiac arrest, spontaneous ventricular arrhythmias, LV thickness >3 cm and an abnormal BP response on exercise testing. Beta-blockers, and non-dihydropiridine calcium channel blockers such as verapamil are used in management to decrease the heart rate, though the use of calcium channel blockers in patients with Hypertrophic Obstructive Cardiomyopathy ("HOCM", a severe subtype of HCM), heart failure (HF) and low blood pressures should be done cautiously. Agents for arrhythmia can be considered for additional symptom relief. Diuretics may be considered for patients with evidence of fluid overload—but cautiously, especially in patients with HOCM. As yet there have been no large-scale randomised trials comparing alcohol septal ablation with surgical myectomy for symptom relief in drug-refractory patients with HCM and the American College of Cardiology and the European Society of Cardiology (ACC/ESC) guidelines recommend surgical myectomy as the primary treatment option, and alcohol ablation in patients with high surgical risks.

Dilated cardiomyopathy (DCM) is characterised by an LV ejection fraction <45 percent with increased (dilated) left ventricular (LV) dimension. DCM presents with dyspnoea, orthopnoea, ankle oedema and weight gain. A viral prodrome may be present. DCM is hereditary in one third of cases (usually autosomal dominant); however, it can be caused by acute viral (usually entero-/adenoviruses) myocarditis leading to chronic inflammation, ventricular remodelling and dysfunction. Five-year survival for DCM patients is about 30 percent and features such as mitral regurgitation or diastolic dysfunction are markers of poor outcome.

Many factors predictive of sudden death in ischaemic LV dysfunction are not predictive in non-ischaemic DCM. A meta-analysis of five trials (1,854 patients with non-ischaemic cardiomyopathy) suggested that ICD therapy reduces all-cause mortality compared with medical therapy (relative risk reduction—31 percent, absolute risk reduction 2 percent per year).

Other rarer causes of cardiomyopathy are arrhythmogenic, restrictive or unclassified. Restrictive cardiomyopathy (RCM) is sub-classified by some researchers into primary (Loeffler's endocarditis, endomyocardial fibrosis) and secondary (e.g. infiltrative causes: amyloidosis, sarcoidosis; storage disorders: haemochromatosis, glycogen storage disorder, Fabry's disease; post-radiation). Loeffler's endocarditis is caused by acute eosinophilic myocarditis with mural thrombosis and fibrotic thickening at the apex of one or both ventricles. Endomyocardial fibrosis is the chronic form. Prognosis depends on aetiology, but is generally poor.

Arrhythmogenic right ventricular cardiomyopathy (ARVC) is caused by fibro-fatty replacement of right ventricular myocytes due to apoptosis, inflammation or a genetic cause (familial in up to half usually with autosomal dominant inheritance). Though ARVC is uncommon (1 in 5,000), it is reported to have regional clustering in places such as northern Italy and Greece.

Unclassified cardiomyopathy includes left ventricular non-compaction (LVNC) and Takotsubo cardiomyopathy. LVNC is caused by embryogenic arrest of normal myocardial maturation resulting in non-compacted myocardial fibres with deep recesses communicating with the LV cavity. Takotsubo cardiomyopathy predominantly affects women and arises from catecholamine surges causing coronary vasospasm and severe apical, mid-LV dysfunction.

For completeness, secondary cardiomyopathies that may overlap with the forms of cardiomyopathy described above include metabolic storage disease causes (e.g. amyloidosis, haemochromatosis), inflammatory causes (e.g. Chagas disease), endocrine causes (e.g. diabetic cardiomyopathy, hyperthyroidism, acromegaly), toxicity causes (e.g. anthracycline chemotherapy, alcohol), neuromuscular (e.g. muscular dystrophy) and nutritional diseases (obesity related). These can be either ischemic or non-ischemic, inherited or acquired (secondary) in various combinations.

As will be readily appreciated, the above classification ontology is but one way in which cardiomyopathies may be ordered. This is particularly the case in view of the fact that many cardiomyopathies are multifactorial in nature, which makes it difficult to place every cardiomyopathy in a discrete class. Specifically recognised cardiomyopathies that may overlap and/or be synonymous with the forms of cardiomyopathy described above include: Arrhythmogenic right ventricular dysplasia (Arrhythmogenic right ventricular cardiomyopathy); Atrial stand still (Atrial cardiomyopathy with heart block); Cirrhotic cardiomyopathy; Congenital cataract—hypertrophic cardiomyopathy—mitochondrial myopathy; Dilated cardiomyopathy; Dilated cardiomyopathy—hypergonadotropic hypogonadism; Dilated cardiomyopathy with ataxia; Early-onset myopathy with fatal cardiomyopathy; Encephalopathy—hypertrophic cardiomyopathy—renal tubular disease; Familial dilated cardiomyopathy; Familial dilated cardiomyopathy with conduction defect due to LMNA mutation; Familial hypertrophic cardiomyopathy; Familial hypertrophic cardiomyopathy (Familial hypertrophic obstructive cardiomyopathy) Familial isolated arrhythmogenic right ventricular dysplasia (Familial isolated arrhythmogenic right ventricular cardiomyopathy); Familial isolated arrhythmogenic right ventricular dysplasia (Familial isolated arrhythmogenic ventricular cardiomyopathy); Familial isolated arrhythmogenic ventricular dysplasia, biventricular form (Familial isolated arrhythmogenic ventricular cardiomyopathy, biventricular form); Familial isolated arrhythmogenic ventricular dysplasia, left dominant form (Familial isolated arrhythmogenic ventricular cardiomyopathy, left dominant form); Familial isolated arrhythmogenic ventricular dysplasia, right dominant form (Familial isolated arrhythmogenic ventricular cardiomyopathy, classic form); Familial isolated arrhythmogenic ventricular dysplasia, right dominant form (Familial isolated arrhythmogenic ventricular cardiomyopathy, right dominant form); Familial isolated dilated cardiomyopathy; Familial isolated dilated cardiomyopathy (Familial or idiopathic dilated cardiomyopathy); Familial isolated hypertrophic cardiomyopathy; Familial isolated hypertrophic cardiomyopathy (Familial isolated hypertrophic obstructive cardiomyopathy); Familial isolated hypertrophic cardiomyopathy (Familial or idiopathic hypertrophic obstructive cardiomyopathy); Familial isolated hypertrophic cardiomyopathy (Hypertrophic obstructive cardiomyopathy); Familial isolated hypertrophic cardiomyopathy (Primitive hypertrophic obstructive cardiomyopathy); Familial isolated restrictive cardiomyopathy; Familial isolated restrictive cardiomyopathy (Familial or idiopathic restrictive cardiomyopathy); Familial restrictive cardiomyopathy; Familial restrictive cardiomyopathy type 1; Familial restrictive cardiomyopathy type 2; Familial restrictive cardiomyopathy type 3; Fatal infantile hypertrophic cardiomyopathy due to mitochondrial complex I deficiency; Fatal infantile hypertrophic cardiomyopathy due to mitochondrial complex I deficiency (Fatal infantile hypertrophic cardiomyopathy due to NADH-CoQ reductase deficiency); Fatal infantile hypertrophic cardiomyopathy due to mitochondrial complex I deficiency (Fatal infantile hypertrophic cardiomyopathy due to NADH-coenzyme Q reductase deficiency); Fatty acid oxidation and ketogenesis disorder with dilated cardiomyopathy; Fatty acid oxidation and ketogenesis disorder with hypertrophic cardiomyopathy; Glycogen storage disease with hypertrophic cardiomyopathy; Glycogen storage disease with hypertrophic cardiomyopathy (GSD with hypertrophic cardiomyopathy); Glycogen storage disease with hypertrophic cardiomyopathy (Glycogenesis with hypertrophic cardiomyopathy); Heart-hand syndrome, Slovenian type (Cardiac conduction disease—dilated cardiomyopathy—brachydactyly); Histiocytoid cardiomyopathy; Histiocytoid cardiomyopathy (Infantile cardiomyopathy with histiocytoid change); Histiocytoid cardiomyopathy (Infantile xanthomatous cardiomyopathy); Histiocytoid cardiomyopathy (Oncocytic cardiomyopathy); Hypertrophic cardiomyopathy; Hypertrophic cardiomyopathy (Obstructive hypertrophic cardiomyopathy); Hypertrophic cardiomyopathy and renal tubular disease due to mitochondrial DNA mutation; Hypertrophic cardiomyopathy and renal tubular disease due to mitochondrial DNA mutation (Hypertrophic cardiomyopathy and renal tubular disease due to mtDNA mutation); Hypertrophic cardiomyopathy due to intensive athletic training; Leigh syndrome with cardiomyopathy; Leigh syndrome with cardiomyopathy (Cardiomyopathy with hypotonia due to cytochrome C oxidase deficiency); Leigh syndrome with cardiomyopathy (Cardiomyopathy with myopathy due to COX deficiency); Lipoatrophy with diabetes, leukomelanodermic papules, liver steatosis, and hypertrophic cardiomyopathy; Lysosomal disease with hypertrophic cardiomyopathy; Lysosomal disease with restrictive cardiomyopathy; Maternally-inherited cardiomyopathy and hearing loss; Maternally-inherited cardiomyopathy and hearing loss (Maternally-inherited cardiomyopathy and deafness); Maternally-inherited cardiomyopathy and hearing loss (tRNA-LYS-related cardiomyopathy—hearing loss); Maternally-inherited mitochondrial hypertrophic cardiomyopathy; Microcephaly—cardiomyopathy; Mitochondrial disease with dilated cardiomyopathy; Mitochondrial disease with hypertrophic cardiomyopathy; Mitochondrial hypertrophic cardiomyopathy with lactic acidosis due to MTO1 deficiency; Naxos disease (Keratosis palmoplantaris with arrythmogenic cardiomyopathy); Naxos disease (Palmoplantar hyperkeratosis with arrythmogenic cardiomyopathy); Naxos disease (Palmoplantar keratoderma with arrythmogenic cardiomyopathy); Neuromuscular disease with dilated cardiomyopathy; Non-familial dilated cardiomyopathy; Non-familial hypertrophic cardiomyopathy; Non-familial rare disease with dilated cardiomyopathy; Non-familial restrictive cardiomyopathy; Peripartum cardiomyopathy; Peripartum cardiomyopathy (Postpartum cardiomyopathy); Progressive sensorineural hearing loss—hypertrophic cardiomyopathy; Progressive sensorineural hearing loss—hypertrophic cardiomyopathy (Progressive neurosensory deafness—hypertrophic cardiomyopathy); Progressive sensorineural hearing loss—hypertrophic cardiomyopathy (Progressive neurosensory hearing loss—hypertrophic cardiomyopathy); Progressive sensorineural hearing loss—hypertrophic cardiomyopathy (Progressive sensorineural deafness—hypertrophic cardiomyopathy); Restrictive cardiomyopathy; Sensorineural deafness with dilated cardiomyopathy; Sensorineural deafness with dilated cardiomyopathy (Neurosensory deafness with dilated cardiomyopathy); Sensorineural deafness with dilated cardiomyopathy (Neurosensory hearing loss with dilated cardiomyopathy); Sensorineural deafness with dilated cardiomyopathy (Sensorineural hearing loss with dilated cardiomyopathy); Severe dilated cardiomyopathy due to lamin A/C mutation; Severe dilated cardiomyopathy due to lamin A/C mutation (Severe dilated cardiomyopathy with or without myopathy); Syndrome associated with dilated cardiomyopathy; Syndrome associated with hypertrophic cardiomyopathy; Tako-Tsubo cardiomyopathy; Tako-Tsubo cardiomyopathy (Ampulla cardiomyopathy); Tako-Tsubo cardiomyopathy (Ballooning cardiomyopathy); Tako-Tsubo cardiomyopathy (Stress cardiomyopathy); Tako-Tsubo cardiomyopathy (Takotsubo cardiomyopathy); Transthyretin-related familial amyloid cardiomyopathy; Transthyretin-related familial amyloid cardiomyopathy (ATTR cardiomyopathy); Transthyretin-related familial amyloid cardiomyopathy (TTR-related amyloid cardiomyopathy); Tubular renal disease—cardiomyopathy; Unclassified cardiomyopathy; Woolly hair-palmoplantar keratoderma-dilated cardiomyopathy syndrome; Woolly hair-palmoplantar keratoderma-dilated cardiomyopathy syndrome (Woolly hair-palmoplantar hyperkeratosis-dilated cardiomyopathy syndrome); Woolly hair-palmoplantar keratoderma-dilated cardiomyopathy syndrome (Wooly hair-palmoplantar keratoderma-dilated cardiomyopathy); and Woolly hair-palmoplantar keratoderma-dilated cardiomyopathy syndrome (Wooly hair-palmoplantar hyperkeratosis-dilated cardiomyopathy syndrome).

Turning now to HCM in more detail, this disease has a prevalence of 1 in 500, which makes it more prevalent overall than an orphan disease. However it is very heterogenous not least in view of the fact that it can be described as idiopathic, familial or acquired.

It is widely accepted that most forms of HCM are caused by mutations in one of the genes currently known to encode different components of the sarcomere. It is usually characterized by left ventricular hypertrophy (LVH) in the absence of predisposing cardiac conditions (e.g., aortic stenosis) or cardiovascular conditions (e.g., long-standing hypertension). The clinical manifestations of HCM range from asymptomatic to progressive HF to sudden cardiac death and vary from individual to individual even within the same family. Common symptoms include shortness of breath (particularly with exertion), chest pain, palpitations, orthostasis, presyncope, and syncope. Most often the LVH of HCM becomes apparent during adolescence or young adulthood, although it may also develop late in life, in infancy, or in childhood.

The diagnosis of HCM is most often established when two-dimensional echocardiography detects LVH in a nondilated ventricle; it can also be established by pathognomonic histopathologic findings in cardiac tissue. Familial HCM (FHCM) without multisystem involvement is diagnosed by family history and molecular genetic testing of any of the 14 genes currently known to encode different components of the sarcomere for which testing is clinically available. FHCM caused by mutation in at least one of the genes currently known to encode different components of the sarcomere is inherited in an autosomal dominant manner.

HCM has been extensively reviewed by Cirino and Ho (2011, http://www.ncbi.nlm.nih.gov.books/NBK1768) and the following has been adapted from their work. As described above, medical management of diastolic dysfunction using beta blockers and non-dihydropyridine calcium channel blockers is used along with medical or surgical management of ventricular outflow obstruction if it exists; important also is achievement and maintenance of sinus rhythm in those with atrial fibrillation; implantable cardioverter-defibrillators (ICDs) are used in survivors of cardiac arrest and those at high risk of cardiac arrest; if HF develops, medical treatment for HF and consideration for cardiac transplantation may be necessary. Prevention of secondary complications may involve anticoagulation in those with persistent or paroxysmal atrial fibrillation to reduce the risk of thromboembolism and antibiotic prophylaxis when necessary. During the pregnancy of a woman with HCM, care by an experienced cardiologist and specialist obstetrician is required.

Monitoring and ongoing management also involves reassessment of risk for sudden cardiac death (SCD) approximately once a year or more frequently based on clinical findings. Patients are advised to avoid competitive endurance training, burst activities (e.g., sprinting), intense isometric exercise (e.g., heavy weight lifting), dehydration, hypovolemia (i.e., use diuretics with caution), and medications that decrease afterload (e.g., ACE-inhibitors, angiotensin receptor blockers, and other direct vasodilators).

To date, HCM is known to be caused by mutation in one of the 14 genes (see Table 1) encoding different components of the sarcomere. More than 900 individual mutations have been identified.

TABLE 1 genes implicated in FHCM (Cirino and Ho (2011, http://www.ncbi.nlm.nih.gov/books/NBK1768/)

| Locus Name | Gene Symbol | Protein Name | % of HCM Caused by Mutations in This Gene | Other disorder phenotypes caused by mutation in same gene |
|---|---|---|---|---|
| CMH1 | MYH7 | Myosin heavy chain, cardiac muscle beta isoform | 40% | Dilated Cardiomyopathy (DCM), Laing distal myopathy |
| CMH4 | MYBPC3 | Myosin-binding protein C, cardiac-type | 40% | DCM |
| CMH2 | TNNT2 | Troponin T, cardiac muscle | 5% | DCM |
| CMH7 | TNNI3 | Troponin I, cardiac muscle | 5% | DCM, restrictive cardiomyopathy |
| CMH3 | TPM1 | Tropomyosin 1 alpha chain | 2% | DCM |
| CMH10 | MYL2 | Myosin regulatory light chain 2, ventricular/cardiac muscle isoform | Unknown | |
| CMH8 | MYL3 | Myosin light polypeptide 3 | 1% | |
| | ACTC1 | Actin, alpha cardiac muscle 1 | Unknown | DCM |
| | CSRP3 | Cysteine and glycine-rich protein 3, muscle LIM protein | Unknown | |
| CMH9 | TTN | Titin | | DCM, Udd distal myopathy |
| | ACTN2 | Alpha-actinin-2 | Unknown | DCM |
| | MYH6 | Myosin heavy chain, cardiac muscle alpha isoform | | DCM |
| | TCAP | Telothonin | | limb-girdle muscular dystrophy, DCM |
| Other genes potentially implicated in HCM | | | | |
| | TNNC1 | Troponin C, slow skeletal and cardiac muscles | Unknown | DCM |

Cirino and Ho describe the sarcomere as the basic contractile unit of the cardiac myocyte. Cardiac contraction occurs when calcium binds the troponin complex (subunits I, C, and T) and α-tropomyosin and releases the inhibition of myosin-actin interactions by troponin I. ATPase activity and binding of actin by the globular myosin head result in conformational changes that bend the neck (also termed the lever arm) and result in the sliding of thick filaments in relation to thin filaments (solid arrows) to generate the power stroke.

As previously stated, HCM is the commonest inherited cardiac disease with an estimated prevalence of 1 in 500. Reports suggest that it is caused by autosomal dominant mutations in the cardiac sarcomeric proteins (FHCM) in 60% of cases. Within FHCM, the most frequent genes to be implicated are myosin heavy chain cardiac muscle beta isoform (MHY7) and cardiac myosin binding protein-C (MYBPC3). Several studies suggest that MYBPC3 mutations are associated with up to 40% of FHCM cases (see Table 1). Accordingly, the prevalence of MYBPC3 related FHCM is arguably >1 in 2000.

According to recent studies examining FHCM associated with MYBPC3, there is a very varied clinical presentation. The disease tends to occur later in life and has a more benign prognosis in comparison with FHCM associated with other sarcomeric protein mutations such as MYH7. This has been used to suggest periodic screening of families with MYBPC3 abnormalities. By determining clinical disease expression, penetrance, and outcomes in a large cohort of patients and relatives with mutations in MYBPC3, these studies demonstrated marked heterogeneity with incomplete, age-related, and gender specific penetrance (Cardiac Myosin Binding Protein-C Mutations in Families With Hypertrophic Cardiomyopathy: Disease Expression in Relation to Age, Gender, and Long Term Outcome Stephen P. Page, Stavros Kounas, et al. Circ Cardiovasc Genet 2012; 5; 156-166). These studies concluded that disease expression (clinical) is heterogeneous and unrelated to mutation type or specific mutation, that disease penetrance is incomplete on average over a carrier's lifetime and that disease penetrance is higher in males than females. Accordingly, because neither mutation type (eg, nonsense, missense, etc) nor specific mutation appeared to predict a particular clinical phenotype in these studies, and because marked phenotypic diversity was seen in families sharing identical mutations, it may be suggested that epigenetic mechanisms (frequently occurring in genes with high mutability) may play a role in the acquired phenotype of FHCM associated with MYBPC3.

There are more than 1,000 causative mutations identified in 20 sarcomere and myofilament related genes associated with HCM and—as stated above—more than 900 associated with 14 genes in the sarcomere. The most frequently occurring gene mutations are associated with MYBPC3. The high density of mutations found in genes associated with HCM may suggest that mechanisms promoting increased mutability play a role in disease prevalence.

DNA methylation is an epigenetic modification that involves the addition of methyl groups to cytosine residues already incorporated into DNA sequences, forming 5-methylcytosine (5MeC). This can either physically prevent transcription factor binding or reduces access through local chromatin condensation, with both processes resulting in gene repression. DNA methylation is regulated by a family of DNA methyltransferase (DNMT) enzymes, one of which, DNMT1, preferentially methylates hemi-methylated DNA and is required to maintain the methylation pattern of the genome in daughter cells during cell division. DNMT3A and DNMT3B are both de novo methylating enzymes, and are responsible for establishing the initial methylation patterns of the genome during development, and their expression re-emerges in disease states. Dysregulation of this process has been extensively studied in cancer.

Differential DNA methylation of CpG sites in two isoforms of MYBPC has been evaluated in studies that also evaluated if the methylation level is gene specific and possibly involved with gene mutability (Meurs and Kuan (Differential methylation of CpG sites in two isoforms of myosin binding protein C, an important hypertrophic cardiomyopathy gene. Environ Mol Mutagen. 2011 March; 52(2):161-4). These studies also evaluated the methylation of the CpGs within the exonic regions of the cardiac (MYBPC3) and skeletal muscle (MYBPC2) isoforms of the myosin binding protein C gene. In the case of MYBPC2, there are no known mutations that lead to the development of FHCM. It was demonstrated that although the mean number of CpGs was similar in the two proteins, the mean methylation level of CpGs was significantly higher in MYBPC3 than MYBPC2 ($P<0.0001$) suggesting that there may be epigenetic involvement resulting in increased genetic mutability.

This hypothesis has been supported by other studies. For example, in one study a significant increase in the number of methylated CpG islands was identified in murine physiologic cardiac hypertrophy (3762±500 vs. 2499±299, $P=0.02$) associated with 741 promoters differentially methylated. Of these, 634 were hypermethylated and 107 were hypomethylated. Promoter DNA methylation data was integrated with the gene expression profiles, and it was discovered that 142 genes showed both altered DNA methylation patterns and expression levels. Gene ontology analysis of these genes reveals an overrepresentation of gene categories involved in actin filament-based process, cytoskeleton organization and programmed cell death (all $P<0.001$). Another study noted that there was methylation in all cytosine residues within CpG dinucleotides found in exons 8, 9, and intron 8 of cardiac troponin T (cTNT) gene in subjects with FHCM. In work that recognizes that epigenetic mechanisms such as microRNA and histone modification are crucially responsible for dysregulated gene expression in HF, a further study evaluated DNA methylation in this setting. They studied ischaemic and idiopathic end-stage cardiomyopathic left ventricular (LV) explants from patients who had undergone cardiac transplantation were profiled compared to normal control. Using a preliminary analysis with methylated-DNA immunoprecipitation-chip (MeDIP-chip), differential methylation loci were then validated by bisulfite-(BS) PCR and high throughput sequencing. It was found that a large population of CpG islands (CGIs) and gene promoters are more significantly hypomethylated in end-stage cardiomyopathic hearts. This study also identified 3 angiogenesis-related genetic loci that were differentially methylated (ARHGAP24, PECAMand AMOTL2). The hypomethylation of the angiomotin-like 2 gene (AMOTL2) and hypermethylation of the 5' promoter region in the platelet/endothelial cell adhesion molecule gene (PECAM1) led to decreased expression of both, whereas hypermethylation within the gene body of Rho GTPase-activating protein 24 (ARHGAP24) favored its expression. Quantitative RT-PCR, found that the expression of these genes differed significantly between CM hearts and normal control ($p<0.01$). There was a correlation between methylation and differential expression of the corresponding gene. It has been noted that this provides the first evidence for a difference in methylation status between human cardiomyopathic hearts and controls.

A subsequent study demonstrated global epigenomic profiles in human cardiomyopathy. DNA methylation and H3K36me3 maps were generated from human hearts, their profiles characterized and it was found that DNA methylation differs between end stage cardiomyopathy and control hearts in CpG islands and gene bodies regions. A significant decrease in global gene promoter methylation also correlated with genes that were upregulated in cardiomyopathy but not with genes that were downregulated, suggesting that demethylation leads to increased expression of the corresponding geno and downregulation of genes in cardiomyopathy occurs independently of promoter methylation.

Of possible relevance to this study is another study in which TNF-α treated HL1 murine atrial cardiomyocytes which exhibited decreased Atp2a2 expression, increased CpG methylation of the gene's promoter, and elevated levels of the DNA (cytosine-5-)-methyltransferase 1 (Dnmt1)—findings combined that suggest that methylation plays an important role in the negative transcriptional regulation of Atp2a2.

It is known that MYBPC3 is hypermethylated, has mutations associated with HCM and when its expression is decreased hypertrophy is worsened. However, for another gene implicated in HCM, ACTA1, increased expression is associated with HCM (mutations of ACTA1 are not known to be associated with HCM, but variations in its level of expression are).

Myocardial fibrosis can be a characteristic feature of HCM and is believed to contribute to the higher risk of sudden cardiac death, arrhythmias and cardiac dysfunction. The fibrosis pattern is associated with increased interstitial and focal fibrosis patterns and can be visualized using cardiac magnetic resonance imaging (MRI) with gadolinium enhancement.

However, fibrosis and hypertrophy are separate but linked processes in the HCM syndrome. For example, it has been shown that one third of HCM patients present with only hypertrophy and do not have evidence of fibrosis on cardiac MRI with late gadolinium enhancement. Nonetheless, the same study also showed that HCM with fibrosis is associated with >3 fold increase in cardiovascular death, unplanned cardiovascular admission, sustained ventricular tachycardia or ventricular fibrillation, or appropriate implantable cardioverter-defibrillator discharge. Furthermore, within the patient cohort with fibrosis, a greater extent of fibrosis was associated with worse outcome.

The cause of myocardial fibrosis in HCM is unclear. Some reports attribute it to premature myocyte death and expansion of the interstitial matrix as a result of the stress created by sarcomere mutations resulting in fibrosis accruing in HCM hearts. Other work has associated the mutations with other pathologic changes such as ischemia—for example compromised coronary flow due to hypertrophy, microvascular dysfunction, increased oxidative stress, and increased metabolic demands imposed by abnormal biophysical properties of mutant sarcomeres resulting in an imbalance of oxygen demand and supply. This can create an ischemic milieu further contributing to the cycle of premature myocyte death and the emergence of focal fibrosis in HCM.

Recent data in mouse models of HCM has shown that sarcomere gene mutations activate proliferative and profibrotic signals in non-myocyte cells from HCM mouse hearts resulting in increased levels of pro-fibrotic proteins including TGFβ resulting in fibrosis.

However, some animal work has also shown that a pro-fibrotic state is already present in animal models when which later develop cardiac hypertrophy before cardiac histologic findings are abnormal. This work is now supported in human patients by recent work that has confirmed the frequent co-existence of fibrosis and hypertrophy and early signals of myocardial fibrosis before clinical hypertrophy is evident. They conclude that elevated levels of serum PICP indicated increased myocardial collagen synthesis in sarcomere-mutation carriers without overt disease and that this profibrotic state preceded the development of left ventricular hypertrophy or fibrosis visible on MRI. Furthermore, while cardiac MRI studies showed late gadolinium enhancement, indicating myocardial fibrosis, in 71% of subjects with overt hypertrophic cardiomyopathy, conversely there was none in the mutation carriers without left ventricular hypertrophy.

Finally, this recent work shows that the pattern and natural history of fibrosis and cardiac dysfunction associated with the two most frequent mutations associated with HCM (MYBPC3 and MYH7) are different. In this work comparing patients with MYBPC3 mutations and MYH7 mutations, but no evidence of HCM, markers of myocardial fibrosis, (PICP levels) and diastolic function (diastolic velocities) were worse in the MYH7 mutation patients. Furthermore, in those patients with the MYBPC3 mutations with HCM, the age of onset of hypertrophy was later, the LVMI was lower, and diastolic function was better than in those patients with MYH7 mutations. These data suggest that MYH7 mutations trigger earlier/more extensive fibrosis and myocardial remodeling than MYBPC3 mutations.

In conclusion: [1] while myocardial fibrosis and hypertrophy often co-exist in patients with HCM, they are distinct pathophysiological features of the disease and in one third of consecutive patients in a large HCM cohort, hypertrophy is evident without fibrosis; [2] this underlines the co-existence but distinct nature of hypertrophy and fibrosis and recent work in HCM mice demonstrates that myocyte expression of sarcomere protein mutations alters gene transcription in non-myocyte cells, inducing proliferation and expression of profibrotic molecules that produce pathologic remodeling and fibrosis in HCM that is dependent on TGFβ; [3] the fibrotic response to sarcomere mutations/abnormalities appears to occur early in the natural history of HCM and this often precedes the development of clinical hypertrophy; [4] while MYBPC3 mutations are associated with HCM, including hypertrophy and fibrosis, there is marked heterogeneity in phenotypic response to mutations of this gene even within families and this could be explained by epigenetic factors such as hypermethylation; [5] based on certain studies, it is known that MYBPC3 is associated with hypermethylation and this is consistent with a high frequency of gene mutations associated with HCM; [6] the hypertrophic myocardium in HCM is in a state of relative hypoxia and this can have important implications for the pathophysiology and natural history of the disease.

With respect to epigenetic therapies, successfully developed epigenetic drugs exist, but they are mostly applied to cancer and haematological diseases. These include (but are not limited to): hypomethylating agents, such as 5-azacytidine (referred to as 5-aza or azacitidine), 5-aza-2'deoxycytidine (referred to as 2'deoxy, 5azaDC, or dectiabine) zebularine; histone deacetylase inhibitors such as suberoylanilide hydroxamic acid; and histone methylation inhibitors such as 3-Deazaneplanocin.

A hypomethylating agent is one that inhibits DNA methylation, and is often referred to as a demethylating agent or a DNA methylation inhibitor. While the terms are used interchangeably in the art, it is at least theoretically possible that hypomethylation/demethylation may also take place by way of mechanisms other than by DNA methylation inhibition. DNA methylation inhibitors (for example, but not limited to, 5-aza, 2'deoxy and zebularine) work by preventing the establishment of new methylation patterns onto newly synthesised DNA during the cell cycle. With every cell division, the methylation pattern of the parent strand is copied to the newly synthesising daughter strand during S-phase of the dividing cell. The enzymes that regulate this process are the DNA methyltransferases (DNMTs). The DNMTs maintain the integrity of the methylation pattern of the genome within each cell. DNA methylation inhibitors prevent or inhibit this process, so that as cells divide they gradually lose their methylation pattern because they are not copied to the newly formed DNA. The DNA methylation inhibitors interact with the DNMT enzymes to achieve this effect. Therefore with continual rounds of cell division, the genes gradually become hypomethylated. Additional hypomethylating mechanisms can occur by which DNA demethylation occurs outside the cell cycle.

Other hypomethylating agents of note include clofarabine and hydralazine. Clofarabine is a cytotoxic purine nucleoside analogue that primarily works by inducing apoptosis. However, the compound is under investigation in clinical trials for its potential hypomethylating effect, and for use in combination with other epigenetic drugs. Clofarabine thus potentially exhibits a dual mode of action, and may be the first of other drugs that may be found to exert a secondary epigenetic mode of action in addition to their primary effect. In clinical trials, this drug has elicited responses in patients with pre-treated relapsed and/or refractory (rr-)ALL, rr-AML, and high-risk myelodysplasia syndrome (MDS).

Hydralazine was originally developed as an oral antihypertensive drug. It is currently being used to treat pregnancy-associated hypertension and is also used in combination with nitrates in the management of HF. Hydralazine has shown the ability to reactivate tumour suppressor gene expression that has been silenced by hypermethylation, both in vitro and in vivo. Hydralazine's extensive previous use as a hypertensive provided the safety and tolerability data that lead to testing in Phase I trial with cancer patients, which confirmed its demethylating ability. It is currently being evaluated in combination therapies with HDAC inhibitors, chemotherapy, or radiation in Phase III trials for haematological and solid tumours.

Bacanamwo et al. Circulation (2007) vol 116, p 124 describes demethylation effects of 5aza on genes associated with hypertension in an Angiotensin II hypertensive disease model, in which an antihypertensive effect of 5aza by putative demethylation effects on genes associated with hypertension such as 1111-HSD2 which was methylated in the arteries and kidneys is reported. The authors conclude the data "suggest that DNA methylation plays a critical role in the coordinate regulation of genes involved in the pathogenesis of hypertension and vascular remodeling." However, hypertension is known to increase hypertrophy and fibrosis and antihypertensive therapies are well known to reduce hypertrophy and fibrosis. The effects described in the present invention are not dependent on hypertension. All genes can be methylated and there is no way to predict that because of the described antihypertensive effects on 11β-HSD2, there could be an antihypertrophic effect of the 5aza independent of hypertension, nor a beneficial effect on, for example, the expression of MYBPC3. Taylor et al New England Journal of Medicine (2004) vol 351 pp 2049-2057, describes the antihypertrophic effects of isosorbide dinitrate and hydralazine in combination. Hydralazine is an antihypertensive agent and antihypertensive agents can reduce hypertrophy and fibrosis. Isosorbide dinitrate has independent pharmacological effects which contribute to and promote BP reduction and protect against myocardial ischemia. There is no evidence that the observed effect on cardiac hypertrophy is related to hydralazine alone and also to epigenetic effects. US A 2011/0319466 describes the use of a HDAC inhibitor (phenylbutyrate) in combination with an ACE inhibitor for the treatment of heart failure, cardiac hypertrophy and cardiac dysfunction. Esha et al. FASEB Journal (2002) vol 16, pA491 describes a DNMT inhibitor (5azaDC) to manage ischemic injury in dogs and an improvementn post-ischemic myocardial function and "scar formation." There is no disclosure of an impact on hypertrophy. Furthermore, hypertrophy can occur in the absence of ischemia and in the case of familial cardiac hypertrophies, the pathophysiological driver is not ischemia.

US A 2012/0014962 describes the antifibrotic effects of DNMT inhibitors on models of liver fibrosis and antifibrotic effects of the drug on cardiac fibrosis and endomyocardial fibrosis. The antifibrotic effects of DNMT inhibitors 5aza and 5azaDC are known, but this is quite distinct to the antihypertrophic effects described in the present application. Kao et al Laboratory Investigation (2011) vol 91, pp 1291-1297 describes the DNMT inhibiting effects of hydralazine on SERCa2. There is no evidence of an antihypertrophic effect independent of SERCAa2 and so it is not possible to ascribe the reduction in cardiac hypertrophy to DNA demethylation, nor could one anticipate the effects of 5aza on MYBPC3. UA A 2009/0105168 describes the use of a DNMT inhibitor for ischemic injury and treatment of hypertrophy and post ischemic injury including cardiac surgery, stroke and myocardial infarction. As mentioned above hypertrophy can occur in the absence of ischemia. In the case of familial cardiac hypertrophies, the pathophysiological driver is often not ischemia.

Fibrosis is often implicated in hypertrophic cardiomyopathy, but there is a substantial number of HCM instances where there is no evidence of fibrosis. Thus, what can be used to treat fibrosis cannot necessarily be used to treat all instances of HCM.

There remains a need for a better understanding of the mechanisms of action of cardiomyopathies, and the possible therapies that may be developed to treat cardiomyopathies in light of such mechanisms of action. There also remains a need for a better understanding of the mechanisms of hypertrophy and/or fibrosis and how possible therapies may be developed in light of such mechanisms of action.

SUMMARY OF THE INVENTION

In one aspect, the present invention provides a hypomethylating agent for use in the prevention or treatment of cardiomyopathy. In one aspect, the hypomethylating agent may comprise 5-Azacytidine or 5-Aza-2'-Deoxycytidine. In an aspect, the hypomethylating agent may be for use in the prevention or treatment of non-ischemic cardiomyopathy. In an aspect the hypomethylating agent may be for use in the prevention or treatment of a cardiomyopathy selected from the group consisting of hypertrophic cardiomyopathy, dilated cardiomyopathy, restrictive cardiomyopathy, arrhythmogenic right ventricular cardiomyopathy and endomyocardial fibrosis. In a further aspect the invention provides a hypomethylating agent for use in the prevention or treatment of cardiomyopathy which is independent of hypertension.

In an aspect, the hypomethylating agent may have the effect of inhibiting the expression of DNA methyltransferase3B.

In another aspect, the present invention provides a method of identifying a therapeutic agent capable of preventing or treating cardiomyopathy comprising testing the ability of putative therapeutic agents to hypomethylate one or more of the 14 genes encoding components of the sarcomere. In one aspect, the method may comprise testing the ability of putative therapeutic agents to hypomethylate the gene cardiac myosin binding protein-C.

In another aspect, the invention provides an agent capable of reducing the expression of, silencing or degrading HIF protein or HIF mRNA for use in the prevention or treatment of cardimyopathy or myocardial fibrosis. The agent may comprise a monoclonal antibody, a peptide or a small molecule capable of interacting with HIF protein and preventing its binding to hypoxia responsive elements within the promoter regions of DNA methyltransferase genes. The agent may also comprise a monoclonal antibody, a peptide, an oligonucleotide or a small molecule capable of binding to hypoxia responsive elements within the promoter regions of DNA methyltransferase genes, thereby preventing binding of HIF to said elements. The agent may comprise the siRNA of SEQ ID 31.

One aspect of the invention comprises prodrugs or pharmaceutically acceptable salts of any of the agents comprised in the invention, or compositions comprising any of said agents and a pharmaceutically acceptable excipient.

In another aspect, the invention comprises a method of identifying a therapeutic agent capable of preventing or treating cardiomyopathy or fibrosis comprising: testing the ability of putative therapeutic agents to reduce the expression of, degrade or silence HIF protein or HIF mRNA; and/or testing the ability of putative therapeutic agents to prevent HIF protein from binding to hypoxia responsive elements within the promoter regions of DNA methyltransferase genes.

A further aspect of the invention comprises a method of preventing or treating cardiomyopathy or myocardial fibrosis comprising the use of a hypomethylating agent as described above.

In another aspect, the invention comprises the use of a hypomethylating agent as described above in a method of treating or preventing cardiomyopathy or myocardial fibrosis.

A further aspect of the invention comprises a method of preventing or treating cardiac hypertrophy or myocardial fibrosis comprising the use of an agent capable of reducing the expression of, silencing or degrading HIF protein or HIF mRNA, or comprising the use of an agent capable of preventing HIF protein from binding to hypoxia responsive elements within the promoter regions of DNA methyltransferase genes. An additional aspect of the invention comprises the use of an agent in such a method. Such agents may include but are not exclusive to, monoclonal antibodies, peptides (whether synthetic or from the animal kingdom), or small molecule inhibitors, that can interact with HIF protein preventing its binding to hypoxia responsive elements (HRE) within DNA methyltransferase (DNMT) promoter regions. Further such agents may include but are not exclusive to agents that can bind to HRE sites on the DNMT promoter regions preventing binding of HIF. Such agents may comprise monoclonal antibodies, peptides (whether synthetic or from the animal kingdom), small molecule inhibitors, or oligonucleotides.

An additional aspect of the invention comprises an agent in accordance with any aspect of the invention for use in the preparation of a medicament for the prevention or treatment of cardiomyopathy, myocardial fibrosis, or other forms of fibrosis. As aspect of the invention further comprises the method of preparing such a medicament, and the use of such an agent in the preparation of such a medicament.

It has not previously been demonstrated that 5-aza and 2'deoxy can modulate cardiac hypertrophy in accepted cardiomyopathic models, something the inventors have now done. Although fibrosis and hypertrophy may co-exist, these are separate disease entities often responding to common stimuli explaining co-existence. Furthermore, it is known that fibrosis occurs as a consequence of abnormal sarcomeric protein expression and that this process heralds a poorer prognosis.

Therefore, the present invention proposes in one aspect that cardiomyopathy associated with abnormal MYBPC3 gene expression arising from gene mutations and hypermethylation results in hypertrophy, fibrosis and a hypoxic environment. It demonstrates for the first time that demethylation using agents such as 5-aza and 2'deoxy increases MYBPC3 expression, and reduces hypertrophy and fibrosis by at least one of the following four mechanisms, or a combination thereof:

(i) direct inhibition of hypermethylation of genes involved in hypertrophy and/or myofibrosis;
(ii) amelioration of relative hypoxia response in the hypertrophic myocardium resulting in reduced HIF induced activation of DNA methyltransferase enzymes which can promote further hypermethylation and activation of hypertrophy and/or fibrosis;
(iii) direct or indirect up-regulation of MYBPC3 gene expression, resulting in reduced activation of a pro-fibrotic response in non-myocyte cells;
(iv) alteration in phosphorylation status of MYBPC3

While hypertrophy and fibrosis are separate disease processes, abnormal expression of sarcomeric genes in the myocardium results in hypertrophy, activates fibrosis through mechanisms described above and results in a more aggressive disease phenotype and poorer prognosis. A therapeutic intervention that could inhibit both hypertrophy and/or fibrosis by one or a combination of the mechanisms described above would be of important clinical value and could present opportunities to manage and perhaps even prevent morbidity and mortality due to cardiomyopathy. Furthermore, the implication of altered MYBPC3 expression and/or other proteins involved in cardiomyopathy extends beyond myocardial hypertrophy and fibrosis. Therapeutic interventions that could inhibit diseases with abnormal methylation patterns could have important use in a number of chronic diseases of other organs such as the eye, gastrointestinal tract, liver, kidney and lung and diseases which are also associated with inflammatory autoimmune conditions. Emerging evidence exemplifies this potential particularly in idiopathic pulmonary fibrosis models, suggesting that DNA hypermethylation changes are reversible with hypomethylating agents such as 5-aza and 2'deoxy resulting disease suppression in-vitro and in-vivo.

The present invention envisages 5-aza, 2'deoxy and other hypomethylating agents for use in the prevention and treatment of cardiomyopathies described and listed in the background section of this application above. The present invention also envisages such hypomethylating agents for use in the prevention and treatment of myocardial fibrosis and other forms of fibrosis. The present invention further envisages therapeutic agents capable of impacting on the inter-action mechanism between HIF protein and the DNMT3b gene promoter, affecting the levels of HIF protein and/or affecting the levels of DNMT3b protein for use in the treatment of cardiomyopathies, myocardial fibrosis and other forms of fibrosis. Further still, the invention envisages a method of treating cardiomyopathy, myocardial fibrosis or another fibrotic condition using any agent comprised in this invention. The invention further envisages the screening for possible therapeutic agents based on the agents' capacity to impact on the HIF-DNMT3b/HRE pathway, or on its capacity of affect the methylation levels or expression patterns of genes implicated in HCM.

BRIEF DESCRIPTION OF THE DRAWINGS

Embodiments of the invention will be described, by way of example only, with reference to the accompanying drawings in which:

FIGS. 1A-1H depicts results illustrating that tissue hypoxia is associated with an enhanced fibrotic expression profile.

FIGS. 2A-2F depicts the results of in vitro hypoxia studies utilising a human primary cardiac fibroblast cell line (HCF)

FIGS. 3A and 3C-3H depicts the results of DNA methylation studies carried out to ascertain whether the pro-fibrotic effects of hypoxia was associated with epigenetic changes within the HCF cells FIGS. 4A-4C depicts the results of an investigation into the mechanism by which hypoxia regulates DNMT3B expression

FIGS. 7A-7C depicts results illustrating that 5aza treatment reverses the pro-fibrotic impact of hypoxia.

FIG. 23 is an illustration of the wild type promoter of DNMT1 showing forward and reverse primer locations and a putative hypoxia response element where HIF protein binds.

FIG. 24 is an illustration of the promoter of DNMT1 showing forward and reverse primer locations and a putative hypoxia response element (HRE) where HIF protein binds, bearing site-directed mutations in the HRE.

FIG. 25 is an illustration of the wild type promoter of DNMT3b showing forward and reverse primer locations and a putative hypoxia response element where HIF protein binds.

FIG. 26 is an illustration of the promoter of DNMT3b showing forward and reverse primer locations and a putative hypoxia response element (HRE) where HIF protein binds, bearing site-directed mutations in the HRE.

DETAILED DESCRIPTION OF THE DRAWINGS

Figure 5A:
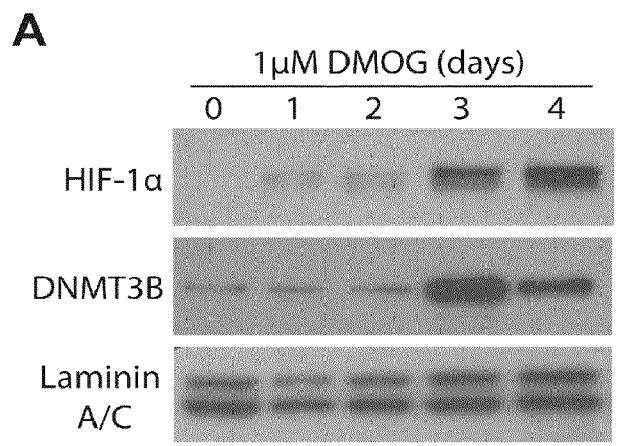
FIG. 5A depicts the results of treatment of HCF cells the HIF-1α stabilisation compound DMOG in normoxia

Example 1—Hypoxia Alters the DNA Methylation Profile of Cardiac Fibroblasts Via HIF-1a Regulation of DNMT3b Methods Human Cardiac Tissue Collection and Handling Human tissue samples were collected from the hearts of 26 stable patients undergoing elective cardiac-bypass surgery. Specifically, right atrial appendages were obtained adjacent to the venous cannulation site in either coronary artery bypass grafting patients (n=18) or valve repair/replacement patients (n=8). All subjects gave written informed consent to participate in the study. The study protocol conformed to the principles of the Helsinki Declaration and received local ethical committee approval. Tissue samples were collected at onset of surgery and immediately divided into two parts and either stored in Aliprotect Tissue Stabilisation Reagent (Qiagen) for subsequent RNA extraction, or formalin-fixed for histological staining.

Cardiac Tissue Analysis

For analysis of gene expression within the myocardial samples, the tissue was first individually disrupted and homogenized using an Ultra Turrax T25 Dispersing Instrument (IKA) before the RNA was extracted using the AllPrep DNA/RNA extraction kit (Qiagen), according to the manufacturer's instructions. First strand cDNA synthesis was carried out using SuperScript II RT (Invitrogen). Quantitative real-time PCR (QPCR) primers were designed so that one of each primer pair was exon/exon boundary spanning to ensure only mature mRNA was amplified. The sequences of the gene-specific primers used are as follows; ASMA, 5'-CGTTACTACTGCTGAGCGTGA-3' (forward) (SEQID 13), 5'-AACGTTCATTTCCGATGGTG-3' (reverse) (SEQID 14); collagen 1 α1 (COL1A1), 5'-GAACGCGTGTCATCCCTTGT-3' (forward) (SEQID 15), 5'-GAACGAGGTAGTCTTTCAGCAACA-3' (reverse) (SEQID 16); collagen 3 α1 (COL3A1), 5'-AACACGCAAGGCTGTGAGACT-3' (forward) (SEQID 17), 5'-GAACGAGGTAGTCTTTCAGCAACA-3' (reverse) (SEQID 18); carbonic anhydrase IX (CAIX), 5'-AGGTCCCAGGACTGGACATA-3' (forward) (SEQID 19), 5'-GAGGGTGTGGAGCTGCTTAG-3' (reverse) (SEQID 20); DNMT1, 5'-TATCCGAGGAGGGCTACCTG-3' (forward) (SEQID 21), 5'-CACTTCCCGGTTGTAAGCAT-3' (reverse) (SEQID 22); DNMT3A, 5'-AGCCCAAGGTCAAGGAGATT-3' (forward) (SEQID 23), 5'-GTTCTTGCACTTTCCCACA-3' (reverse) (SEQID 24); DNMT3B, 5'-TCAGGATGGGAAGGAGTTTG-3' (forward) (SEQID 25), 5'-CTGCAGAGACCTCGGAGAAC-3' (reverse) (SEQID 26). QPCR reactions were normalized by amplifying the same cDNA with beta-2-microglobulin (B2M) primers, 5'-AGGCTATCCAGCGTACTCCA-3' (forward) (SEQID 27), 5'-CCAGTCCTTGCTGAAAGACA-3' (reverse) (SEQID 28).

QPCR was performed using Platinum SYBR Green qPCR SuperMix-UDG (Invitrogen). Amplification and detection were carried out using Mx3000P System (Stratagene). The PCR cycling program consisted of 40 three-step cycles of 15 seconds/95° C., 30 seconds/TA and 30 seconds/72° C. Each sample was amplified in duplicate. In order to confirm signal specificity, a melting program was carried out after the PCR cycles were completed.

For analysis of interstitial collagen within the myocardial sample, formalin-fixed tissue was paraffin-embedded and stained using a Masson's trichrome (MTC) Stain Kit (Dako) optimised for use on an Artisan staining system according to the manufacturer's instructions.

Manual Scoring of MTC Stained Cardiac Biopsies

Microscope slides containing 8 µM thick sections of myocardial tissue stained with MTC were examined by a pathologist (OSE) and manually assessed for the degree of fibrosis in a blinded fashion. MTC for collagen type I detection (fibrosis) was graded from 1 to 5, where 1 is the least and 5 is the most severe interstitial fibrosis. Only interstitial fibrosis was considered, where invasive fibrosis with muscle replacement or compression would count. Subendocardial or epicardial fibrosis were excluded.

Automated Image Analysis of MTC Stained Cardiac Biopsies

The Aperio ScanScope XT Slide Scanner (Aperio Technologies) system was used to capture whole slide digital images with a 20× objective. Automated image analysis was performed using Imagescope (Aperio). A positive pixel count algorithm was used to automatically quantify the area occupied by stain colours within each scanned slide image. Calibration of individual staining patterns was performed by specifying the requisite colour (range of hues and saturation) and limits for the desired intensity range. Required input parameters for each stain were based on the HSI (Hue, Saturation and Intensity) colour model. To detect the blue colour of collagen with MTC stain, a hue value of 0.66 was specified. The equivalent value for detection of red stained myocytes was 0.0. The default hue width value of 0.5 was used to allow inclusion of a moderate range of colour shades. A collagen volume fraction was calculated based on the percent of blue collagen staining quantified within a tissue section.

Primary Cell Culture

Primary human cardiac fibroblast cells from the adult ventricle (HCF) were purchased from ScienCell Research Laboratories. Primary cells were derived from a single female donor aged 20. Until required for experiments, cells were cultured and maintained in Dulbecco's modified eagles medium (DMEM) (Gibco), supplemented with 10% Fetal Bovine Serum (Gibco) and penicillin-streptomycin antibiotics (Gibco) in a 5% CO2 humidified incubator kept at 37° C.

Cell Culture Treatments

Where indicated, HCF cells were exposed to a 1% oxygen environment for up to 8 days using a hypoxic chamber (Coy Laboratories). The effects of 10 ng/ml recombinant TGFβ1 treatment (R&D Systems) under these conditions were investigated. When required, cells were treated for 24 hours with 1 mM of the prolyl hydroxylase inhibitor DMOG (Sigma) to simulate hypoxia through the induction of HIF under normoxic conditions.

Quantitative Flow Cytometry

The impact of hypoxia on HCF cells global methylation profile was investigated using an antibody specific to methylated DNA and quantified using flow cytometry. Briefly, HCF cells exposed to either normoxia (21% oxygen) or hypoxia (1% oxygen) were fixed in Carnoy's solution prior to 60 minutes acid hydrolysis in 1M HCl at 37° C. Following this DNA denaturation step, cells were immunostained using anti-5'methylcytidine (5MeC) monoclonal antibody (Eurogentec). IgG1 negative controls were used at the same concentration as the primary antibody. Secondary immunostaining was conducted using an FITC conjugated rabbit anti-mouse secondary antibody (Dako). Analysis was performed on a CYAN flow cytometer and results assessed using SUMMIT software (Dako).

Quantitative Real-Time PCR Analysis of Primary HCF Cells

Gene expression changes were measured in HCF cells using QPCR as described in human cardiac tissue analysis methods section. RNA isolation from cells was achieved using NucleoSpin RNA II Kit (Macherey-Nagel). QPCR data was analysed using the delta delta CT method.

Western Blotting

Whole cell protein lysates were generated using RIPA Lysis Buffer (Millipore), containing a protease inhibitor cocktail (Roche). Nuclear protein extracts were obtained using the Ne-PeR Nuclear and Cytoplasmic extraction Reagents, according to manufacturer's instructions (Pierce Biotechnology). Protein concentrations were determined using the BCA Protein Assay Kit (Pierce). 10-20 µg of protein lysates were denatured, reduced and resolved on SDS-polyacrylamide gels by SDS-PAGE before transfer onto 0.45 µm pore size Immobilon-P polyvinylidene fluoride (PVDF) membranes (Millipore).

Membranes were incubated with blocking buffer (TBS, 0.25% Tween-20, 0.1% serum from species that secondary antibody was raised in, and 5% fat free skimmed milk) for 1 hour at room temperature. Membranes were subsequently probed overnight with either anti-ASMA (Sigma), anti-collagen 1, anti-DNMT3B (Imgenex), or anti-hypoxia inducible factor 1α (HIF-1α) (Novus Biologicals). Detection of the specific binding of the primary antibody was achieved using HRP-conjugated secondary antibodies, followed by signal detection with Immobilon Western chemiluminescent HRP substrate (Millipore) according to the manufacturer's instructions. Anti-alpha tubulin (Sigma) was used to verify equal loading.

Generating a Functional and Mutated DNMT3B Luciferase Construct

A 250 bp fragment of the DNMT3B promoter containing a putative hypoxia response element (HRE) was cloned and inserted into a pGL3 luciferase construct (Promega), generating pDNMT3B-Luc. In addition, a mutated version of this construct was created by site-directed mutagenesis using QuikChange II Site-Directed Mutagenesis Kit (Stratagene) to mutate the putative HRE within the DNMT3B promoter. Specifically, 2 cytosine bases within the putative HRE were replaced with adenine bases, generating pDNMT3B-ΔHRE-Luc. DNA sequencing was used to confirm the presence of the mutation. Either pDNMT3B-Luc, pDNMT3B-ΔHRE-Luc, or empty vector was subsequently transiently transfected into Hela cells using FUGENE HD (Promega). 24 hours post transfection, cells were either exposed to 1% oxygen for 24 hours, or left in normoxia (21% oxygen). The degree of DNMT3B promoter activity was quantified using the luciferin/luciferase bioluminescence assay following cell lysis with Passive Lysis Buffer (Promega) and incubating with Luciferase Assay Reagent (Promega), with luciferase activity measured on a GloMax 20/20 Luminometer (Promega).

siRNA Targeted DNMT3B Knock Down

HCF cells were transfected with either 20 nM siDNMT3B of the sequence 5'-AGAUGACGGAUGCCUAGAGUU-3' (SEQID 31), or control siRNA using DharmaFect4 transfection reagent (Dharmacon). Transfected cells were incubated for 12 hours prior to hypoxic exposure of 1% oxygen for 4 days, or left in normoxia (21% oxygen). To ensure DNMT3B levels remained low over the time course, siRNA was replenished on day 2. The impact or 10 ng/ml TGFβ under these experimental conditions was also investigated.

DNA Demethylation with 5-aza-2'-deoxycytidine

For demethylation analysis, cells were treated with 1-5 μM 5-aza-2'-deoxycytidine (5-azadc; Sigma) for up to eight days. The effect of global DNA methylation inhibition on pro-fibrotic protein expression was assessed using Western blotting.

Results

Myocardial Tissue Hypoxia is Associated with an Enhanced Fibrotic Gene Expression Profile.

Following ethical approval and informed patient consent, human right atrial tissue samples were collected from the hearts of 26 patients undergoing elective cardiac-bypass surgery. RNA was extracted from this tissue and was used to look at the relationship between hypoxia and collagen production using quantitative real-time PCR. The degree of carbonic anhydrase IX (CAIX) expression was used as a validated surrogate marker for cardiac tissue hypoxia (Holotnakova 2008). A significant positive correlation between collagen 1 gene expression with CAIX was detected (r=0.50, p<0.01), as highlighted in FIG. 1B. Relative CAIX gene expression levels also correlated positively with ASMA (r=0.42, p<0.05), FIG. 1A. Collagen 3 gene expression was not statistically associated with changes in CAIX expression, although a positive trend was observed (r=0.35, p=0.07).

Tissue Hypoxia is Associated with Increased Collagen Deposition

The degree of collagen deposition within right atrial tissue samples was assessed using Masson's trichrome (MTC) staining. Examples of myocardial tissue stained with MTC can be observed in FIG. 1D, with positive blue staining for collagen being evident, and myocytes staining red. This figure highlights examples of both interstitial and perivascular fibrosis. Two methods were used to analyse the collagen content within the MTC stained slides, namely, digital quantification of positive pixels (FIG. 1E, an example were the positive pixel algorithm has been applied to a MTC stained slide generating a mark up image detailing the positive blue pixels representing collagen) and blinded manual scoring by a Pathologist (OSE) (FIG. 1F, examples of manual scoring images grading collagen deposition between 0-5).

The relationship between collagen deposition and hypoxia was assessed by dividing the MTC slides into two groups based on median CAIX gene expression levels. Results indicate that increased tissue hypoxia (higher CAIX expression) was associated with a significant increase in collagen (p<0.05). This was observed in both the automated digitally analysed positive pixel quantification of collagen (FIG. 1G) and the blinded manual scoring of MTC staining (FIG. 1H).

These results indicate that the degree of hypoxia within myocardial tissue is associated with increased expression of the pro-fibrotic genes ASMA and collagen 1, as well as increased deposition of fibrillar collagen protein. As the likely source of the increased collagen within the myocardium is the cardiac fibroblast we undertook in vitro hypoxia studies utilising a human primary cardiac fibroblast cell line (HCF). HCF cells were cultured in either 21% oxygen or 1% oxygen for up to 8 days. Culturing cells in 1% oxygen stabilised nuclear HIF-1α, indicating that the cells were experiencing a hypoxic environment, FIG. 2A. Under these conditions, an increase in cell proliferation was observed, another pathological feature of fibrosis, FIG. 2B. Using quantitative real-time PCR, a significant increase in both ASMA and collagen 1 gene expression was detected at 4 and 8 days post hypoxia, compared with cells grown under normoxia, FIGS. 2C and 2D. Interestingly, the pro-fibrotic effects of TGFβ1 treatment was enhanced in hypoxia. TGFβ1 treatment of HCF significantly increased ASMA and collagen 1 gene expression, and this was further enhanced if the cells were exposed to 8 days hypoxia, FIGS. 2E and 2F, respectively.

To determine whether the pro-fibrotic effects of hypoxia was associated with epigenetic changes within the HCF cells, DNA methylation studies were carried out. Global DNA methylation was analysed in cells exposed to either 21% oxygen, 1% oxygen for 4 days, or 1% oxygen for 8 days. Application of an antibody directed to methylated DNA (anti-5MeC) and quantification using flow cytometry revealed significant DNA hypermethylation in hypoxic cells (p<0.001), FIG. 3A. Confirmation of specific nuclear staining was achieved using immunofluorescent microscopy, as highlighted in FIG. 3B, with specific nuclear anti-5MeC positivity over a background of the blue nuclear counterstain DAPI. To investigate possible mechanisms of hypoxia induced DNA hypermethylation, the enzymes that catalyze this process were quantified, namely the DNA methyltransferases (DNMT). The gene expression levels of DNMT1, the enzyme primarily responsible for maintaining the methylation status of daughter cells during cell cycle, and the de novo methylating enzyme DNMT3B, were both significantly up-regulated as early as 24 hours following exposure to a 1% hypoxic environment (p<0.001), FIGS. 3C and 3E. Levels of the de novo methylating enzyme DNMT3A was unchanged, FIG. 3D. Western blot analysis of hypoxic nuclear extracts showed that DNMT3B protein was significantly up-regulated in hypoxia, suggesting a possible role in regulating the global changes in DNA methylation in hypoxia. Interestingly, when examining the human cardiac tissue samples, DNMT3B gene expression levels significantly correlated with CAIX levels (r=0.50, p<0.001), FIG. 3F.

The mechanism by which hypoxia regulates DNMT3B expression was explored due to the potential importance of this de novo methylating enzyme in directing epigenetic changes and susceptibility to hypoxia induced fibrosis. Following analysis of the DNMT3B promoter, a consensus sequence for a HIF-1α binding site, referred to a hypoxia response element (HRE) was identified. Accordingly, this hypoxia mediated transcription factor posed as a likely candidate for regulating DNMT3B expression. To investigate this further, a luciferase expression construct containing the human DNMT3B promoter was generated (pDNMT3B-Luc). An additional construct was generated were the HIF-1α binding site was mutated (pDNMT3B-ΔHRE-Luc). Hela cells were selected as a suitable vehicle to investigate hypoxia regulation of DNMT3B as they possess a functional HIF-1α responsive pathway when exposed to 1% hypoxia, as indicated by nuclear protein stabilisation, FIG. 4A. Hela cells were utilised and transfected with either a luciferase construct with a functional or HRE mutated DNMT3B promoter sequence. Cells were cultured in normoxia or 1% hypoxia for 24 hours, prior to analysis of luciferase activity. Results indicate that the DNMT3B promoter activity is increased 3-fold in hypoxia (p<0.05), FIG. 4B. Hypoxia mediated DNMT3B promoter activity was significantly attenuated when the HIF-1α binding site was mutated (p<0.001), FIG. 4C.

As supportive evidence for a role for HIF-1α in regulating DNMT3B expression in hypoxia, HCF cells were treated with the HIF-1α stabilisation compound DMOG in normoxia. As highlighted in FIG. 5A, DMOG treatment stabilises nuclear HIF-1α protein expression, and also results in increased expression of DNMT3B.

Collectively, these data indicate that hypoxia induced expression of DNMT3B in cardiac fibroblast cells is at least in part regulated by the hypoxia inducible transcription factor HIF-1α.

Figure 6:
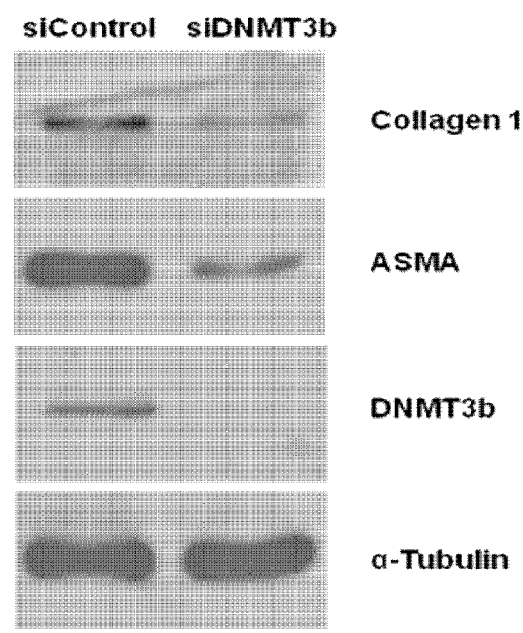
FIG. 6 depicts results illustrating that siRNA mediated reduction in DNMT3B (siDNMT3B) resulted in reduced expression levels of the pro-fibrotic proteins ASMA and Collagen 1.
Figure 8:
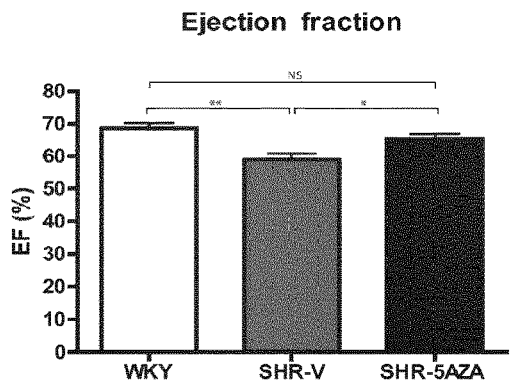
FIGS. 8-11 depict the effect of 5AZA treatment on echocardiographic parameters. Ejection fraction (EF) was significantly improved in SHR-5AZA compared with SHR-V. A significant reduction in cardiac hypertrophy was observed. 5AZA treatment reduced left ventricular mass index (LVMi) and the interventricular septum diameter. Diastolic dysfunction was observed in SHR-V, as measured by E prime (E') and this was significantly improved with 5AZA treatment. Results represent mean and standard error of the mean. * $p<0.05$,  $p<0.01$, * $p<0.001$.
Figure 11:
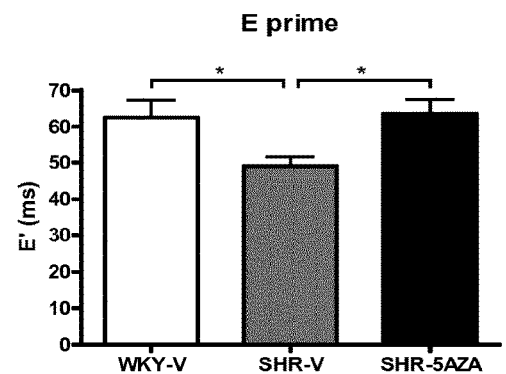
Figure 9:
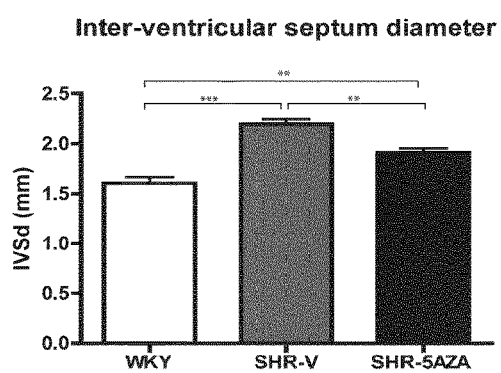

Based on these results, the potential anti-fibrotic impact of blocking either hypoxia induced HIF-1α expression or DNMT3B expression on the pro-fibrotic effects of hypoxia on HCF was investigated. These experiments were carried out using siRNA to prevent/reduce DNMT3B expression. Human cardiac fibroblast cells were transfected with either siDNMT3B or control siRNA using. Transfected cells were analysed four days later using Western blotting to quantify cellular levels of collagen 1 and alpha smooth muscle actin (ASMA). siRNA targeted DNMT3B knock down resulted in a significant reduction in expression of pro-fibrotic proteins including ASMA and collagen 1. Successful siRNA knockdown of DNMT3B was confirmed by Western blotting (FIG. 6). Alpha tubulin was utilised as a loading control.

Treating hypoxic fibroblasts with the DNMT inhibitor 5-aza2dC inhibited the pro-fibrotic effects of TGFβ, one of the most potent pro-fibrotic agonists. 5-aza2dC significantly reduced expression of ASMA, collagen 1 and collagen 3.

Discussion

The detrimental impact of ischemia on the structure and function of the myocardium is well acknowledged. Initial cardiac responses to regional hypoxia, usually after myocardial infarction or following prolonged coronary artery disease are organ protective. However, chronic insults or maladaption to the pathophysiological process can lead to reactive cardiac fibrosis and over time may potentially lead to heart failure 1, 3. The importance of this led us to investigate the relationship between hypoxic myocardial tissue and fibrosis, and to determine whether hypoxia can regulate the fibrotic phenotype in cardiac fibroblast cells. We also sought to examine whether any hypoxia induced pro-fibrotic responses were related to changes in the epigenetic profile of cardiac fibroblast cells.

Following ethical approval, we acquired atrial myocardial tissue samples from 26 patients undergoing elective cardiac bypass surgery for either coronary artery bypass grafting or mitral valve repair/replacement. With this tissue we were able to look at the relationship between the degree of tissue hypoxia and fibrosis. The extent of myocardial tissue hypoxia was assessed by quantifying the gene expression levels of carbonic anhydrase IX (CAIX). CAIX is involved in cell adhesion and pH regulation with its expression being controlled by hypoxia inducible factor 1 (HIF-1). The importance of CAIX within the hypoxic myocardium has been shown 8. Although HIF-1 is the main mediator of hypoxic responses, its fluctuating stability and rapid degradation would have proved difficult to study in tissue samples collected at time of surgery, therefore CAIX was adopted as a surrogate marker of hypoxia 9, 10. Analysis of the myocardial tissue highlighted a significant positive correlation between gene expression levels of CAIX with both collagen 1 and the myofibroblast differentiation marker alpha-smooth muscle actin (ASMA). Collagen 3 gene expression did not significantly correlate, however a close relationship was observed. To further investigate this, the cardiac tissue samples were stained with Masson's trichrome blue (MTC) in order to quantify fibrillar collagen 1 protein deposition. Staining for collagen, blue in appearance, was quantified using two approaches, namely automated digital analysis which involved applying a positive pixel algorithm to quantify blue pixels within digitalised stained sections, and a manual blinded scoring method carried out by an experienced clinical pathologist (OSE). Using the median CAIX expression level, the tissue cohort was divided into low and high CAIX expressers, signifying low and high tissue hypoxia. Using this division, the degree of collagen deposition was compared. Using automated quantification, a significantly higher level of collagen deposition was detected in the more hypoxic tissue (high CAIX) and these findings were confirmed by the blinded manual scoring. In light with previously published work these findings support other studies exploring the impact of hypoxia and fibrosis.

As the main source of enhanced ASMA and collagen with the degree of hypoxia in cardiac tissue is the fibroblast, we carried out in vitro studies utilising a primary human cardiac fibroblast cell line (HCF) and subjecting it to hypoxia. In support with the myocardial tissue findings, we exposed HCF cells to 1% oxygen for up to 8 days. Importantly, hypoxia stabilised HIF-1α protein under these conditions demonstrating the cells were experiencing a hypoxic environment. Interestingly, we also observed an increase in cell proliferation in hypoxia, a process that could contribute to the overall fibrotic burden in vivo. Other than an increase in fibroblast numbers within fibrotic diseases (increased proliferation or reduced apoptosis), an enhanced profibrotic phenotype is an important contributor to the disease with myofibroblast differentiation and increased extracellular matrix deposition. Here we report an increase in collagen 1 and ASMA expression in fibroblasts exposed to chronic hypoxia (1%, 8 days). Importantly, these cells are also more responsive to exogenous TGFβ1 treatment, exhibiting greater levels of collagen 1 and ASMA induction. Although these results are limited to studying collagen, ASMA, and proliferation as indicators of chronic hypoxia generating a pro-fibrotic phenotype, it is likely that these cellular responses involve multiple alterations in gene expression profiles. As such, we sought to determine whether these findings occurred on a background of epigenetic changes, and thus providing a potential platform to support fibrogenesis.

The importance of epigenetics in cardiovascular disease is becoming ever apparent, with some studies exploring the impact of histone modifications on gene expression in diseases. However, studies into the impact of epigenetic modifications in cardiac fibroblasts are limited, particularly investigations into DNA methylation changes and subsequent pro-fibrotic phenotypes. Given the importance of this epigenetic phenomenon, and previously published literature highlighting that hypoxia can impact the epigenetic machinery, including DNA methylation in cancer this study set out to examine whether hypoxia can alter the DNA methylation profile of cardiac fibroblast cells. As highlighted in FIG. 3A, it was found that chronic hypoxia significantly increased global DNA methylation within the genome of cardiac fibroblast cells. Subsequent analysis of the DNA methyltransferase enzymes (DNMT) revealed that both DNMT1 and DNMT3B gene and protein expression was increased, highlighting a potential mechanism by which hypoxia can hypermethylate the DNA of cardiac fibroblast cells. Interestingly, DNMT1 and DNMT3B gene expression levels within the cardiac tissue significantly correlated with CAIX levels, highlighting that the in vitro relationship between hypoxia and DNMTs are also apparent in vivo.

During embryogenesis, expression levels of the de novo methylation enzyme DNMT3B are high when the methylation pattern of the genome is being established. Whereas in normal healthy adult tissue DNMT3B expression is usually low, however, increased expression has been implicated in the pathogenesis of numerous diseases, including cancer. Therefore, its re-emergence in disease states is likely causing pathological DNA methylation and aberrant gene silencing. It was therefore examined whether there was a direct role for DNMT3B in hypoxia mediated cardiac fibrosis. Upon examination of the DNMT3B promoter, a putative hypoxia response element (HRE) was discovered, providing a mechanism by which hypoxia can drive its expression via the transcription factor HIF-1α. Three approaches were undertaken to confirm this theory; (I) a study generating DNMT3B promoter driven luciferase constructs with either a functional (pDNMT3B-Luc) or mutated (pDNMT3B-ΔHRE-Luc) HRE site, (II) a study looking at the impact of siHIF-1α, and (III) a study using the compound DMOG to stabilise HIF-1α in normoxia. As shown in FIG. 4, Hela cells transfected with pDNMT3B-Luc exhibit a significant increase in luciferase expression compared with cells maintained in normoxia. Importantly, when the HRE site is mutated, there is a significant blunting in luciferase activity. Of note, DNMT3B up-regulation is not completely abolished, suggesting the possibility that additional hypoxia mediated transcription factors may contribute to DNMT3B regulation. A role for HIF-1α in regulating DNMT3B is further supported by siRNA and DMOG experiments, as shown in FIG. 5.

Collectively, all three approaches confirm that hypoxia mediated up-regulation of DNMT3B is regulated by the hypoxia inducible transcription factor HIF-1α. The importance of this stems well beyond the scope of cardiac fibrosis and into the realms of other diseases, including cancer biology, and other fibrotic entities.

Having shown that hypoxia is associated with a pro-fibrotic phenotype, which occurs against a background of epigenetic changes, including HIF-1α mediated DNMT3B up-regulation, it was sought to determine whether global demethylation or a DNMT3B targeted approach could be potentially anti-fibrotic. Firstly, the impact of reversing DNA methylation on cellular responses to the pro-fibrotic cytokine TGFβ was investigated. Using the DNA demethylation drug 5-aza-2-deoxycytidine, it was shown that responses to TGFβ were significantly reduced. Specifically, reduced expression of ASMA, collagen 1 and collagen 3 was observed. The impact of directly targeting DNMT3B was also investigated using siRNA. Results show that by reducing or suppressing DNMT3B expression protein levels of ASMA and collagen 1 are significantly reduced. Collectively these novel data highlight the potential use of epigenetic mediated therapies, specifically those that target DNA methylation, to reduce, prevent or reverse cardiac fibrosis.

Characteristics of the patients from whom cardiac tissue was obtained are summarized in Table 2. Relative tissue hypoxia was determined based on above and below the median gene expression levels of the hypoxic marker CA9.

TABLE 2

Characteristics of the patients from whom cardiac tissue was obtained. Values are mean ± SD, median (25th:75th percentiles) or n (%).

| Demographics | Total Population | Hypoxic tissue (High CAIX) | Normoxic tissue (Low CAIX) |
| --- | --- | --- | --- |
| N | 26 | 13 | 13 |
| Age, yr | 72 ± 10 | 72 ± 9 | 72 ± 11 |
| Gender, male | 18 (69%) | 9 (69%) | 9 (69%) |
| SBP, mmHg | 134 ± 6 | 134 ± 6 | 132 ± 7 |
| DBP, mmHg | 78 ± 7 | 76 ± 6 | 80 ± 7 |
| BMI, kg/m$^2$ | 27 ± 3 | 27 ± 3 | 27 ± 3 |
| Atrial Fibrillation | 5 (19%) | 2 (15%) | 3 (23%) |
| Diabetes Mellitus | 5 (19%) | 3 (23%) | 2 (15%) |
| Smoking History | 10 (38%) | 7 (54%) | 3 (23%) |
| Hypercholesterolemia | 9 (35%) | 6 (46%) | 3 (23%) |
| Coronary Artery Disease | 20 (77%) | 10 (77%) | 10 (77%) |
| Valvular Heart Disease | 12 (46%) | 5 (38%) | 7 (54%) |
| Hypertension | 9 (35%) | 4 (31%) | 5 (38%) |
| RAAS Inhibitor | 12 (41%) | 6 (46%) | 6 (46%) |
| Beta-Blocker | 16 (55%) | 9 (69%) | 7 (54%) |
| Statin | 16 (55%) | 11 (85%) * | 5 (38%) |
| Creatinine, μmol/l | 90 ± 13 | 90 ± 4 | 90 ± 17 |

TABLE 2-continued

Characteristics of the patients from whom cardiac tissue was obtained. Values are mean ± SD, median (25th:75th percentiles) or n (%).

| Demographics | Total Population | Hypoxic tissue (High CAIX) | Normoxic tissue (Low CAIX) |
|---|---|---|---|
| BNP, pg/ml | 104 (17:127) | 84 (15:116) | 135 (26:171) |
| LVEF, % | 60 ± 7 | 60 ± 7 | 60 ± 8 |
| LVIDd, mm | 53.0 ± 5.0 | 53.0 ± 4.8 | 55.0 ± 5.2 |
| IVS, mm | 9.7 ± 1.5 | 9.6 ± 1.3 | 9.9 ± 1.7 |
| PW, mm | 10.7 ± 1.6 | 10.5 ± 2.0 | 11.0 ± 1.1 |
| E/e' | 8.7 ± 2.8 | 8.7 ± 3.0 | 8.6 ± 2.6 |
| LAVI, mls/m$^2$ | 28.4 ± 4.4 | 28.1 ± 5.2 | 28.6 ± 3.4 |

SBP/DBP, systolic and diastolic blood pressure;
BMI, body mass index;
RAAS Inhibitor, renin angiotensin system inhibitor;
BNP, b-type natriuretic peptide;
LVEF, left ventricular ejection fraction;
LVIDd, left ventricular end diastolic dimension;
IVS, intraventricular septum;
PW, posterior wall;
E/e', ratio of mitral early diastolic flow velocity over tissue Doppler lateral mitral annular lengthening velocity;
LAVI, left atrial volume index.

Example 2—Epigenetic Therapy for the Treatment of Cardiac Fibrosis and Hypertrophy Methods Primary Cell Culture and Treatments Primary human cardiac fibroblast cells from the adult ventricle (HCF) were purchased from ScienCell Research Laboratories. Cells were cultured and maintained in Dulbecco's modified eagles medium (DMEM) (Gibco), supplemented with 10% Fetal Bovine Serum (Gibco) and penicillin-streptomycin antibiotics (Gibco) in a 5% $CO_2$ humidified incubator kept at 37° C. When required, HCF cells were treated for up to 8 days with either 10 ng/ml human recombinant transforming growth factor beta 1 (TGFβ1) (R&D Systems), 1 µM 5-azacytidine (5-aza) (Sigma), or with both compounds simultaneously.

Quantitative Real-Time PCR

RNA isolation from HCF cells was achieved using NucleoSpin RNA II Kit (Macherey-Nagel). First strand cDNA synthesis was carried out using SuperScript II RT (Invitrogen). Quantitative real-time PCR (QPCR) primers were designed so that one of each primer pair was exon/exon boundary spanning to ensure only mature mRNA was amplified. The sequences of the gene-specific primers used are as follows; ASMA, 5'-CGTTACTACTGCTGAGCGTGA-3' (forward), 5'-AACGTTCATTTCCGATGGTG-3' (reverse); collagen 1 α1 (COL1A1), 5'-GAACGCGTGT-CATCCCTTGT-3' (forward), 5'-GAACGAGGTAGTC-TTTCAGCAACA-3' (reverse); collagen 3 α1 (COL3A1), 5'-AACACGCAAGGCTGTGAGACT-3' (forward), 5'-GAACGAGGTAGTCTTTCAGCAACA-3' (reverse). QPCR reactions were normalized by amplifying the same cDNA with beta-2-microglobulin (B2M) primers, 5'-AGGCTATCCAGCGTACTCCA-3' (forward), 5'-CCAGTCCTTGCTGAAAGACA-3' (reverse).

QPCR was performed using Platinum SYBR Green qPCR SuperMix-UDG (Invitrogen). Amplification and detection were carried out using Mx3000P System (Stratagene). The PCR cycling program consisted of 40 three-step cycles of 15 seconds/95° C., 30 seconds/TA and 30 seconds/72° C. Each sample was amplified in duplicate. In order to confirm signal specificity, a melting program was carried out after the PCR cycles were completed. Relative fold changes in gene expression was calculated using the delta delta CT method.

Western Blotting

Whole cell protein lysates were generated using RIPA Lysis Buffer (Millipore), containing a protease inhibitor cocktail (Roche). Protein concentrations were determined using the BCA Protein Assay Kit (Pierce). Protein lysates were denatured, reduced and resolved on SDS-polyacrylamide gels by SDS-PAGE before transfer onto 0.45 µm pore size Immobilon-P polyvinylidene fluoride (PVDF) membranes (Millipore).

Membranes were incubated with blocking buffer (TBS, 0.25% Tween-20, 0.1% serum from species that secondary antibody was raised in, and 5% fat free skimmed milk) for 1 hour at room temperature. Membranes were subsequently probed overnight with anti-ASMA (Sigma). Detection of the specific binding of the primary antibody was achieved using HRP-conjugated secondary antibodies, followed by signal detection with Immobilon Western chemiluminescent HRP substrate (Millipore) according to the manufacturer's instructions. Anti-alpha tubulin (Sigma) was used to verify equal loading.

5-azacytidine Treatment of a Rat Model of Hypertensive Heart Disease

Approval from the local Animal Research Ethics Committee was sought and obtained to investigate the antifibrotic impact of 5-aza on cardiac function and fibrosis. Male spontaneously hypertensive rats (SHR) and their normotensive counterpart Wistar Kyote rats (WKY) were purchased from Charles River and utilised for the study. From 10 weeks of age, the animals received alternate day intraperitoneal injection of either PBS (vehicle) or 5-aza (10 mg/kg) for 12 weeks. The 5-aza was purchased from Sigma, diluted in sterile PBS and filtered through a 0.22 µm filter. Aliquots were stored at −20° C. and were used within 5 days of reconstitution. The study design consisted of three groups of 10 animals; group 1 included 10 SHR rats who received 5-aza (SH R-5-aza); group 2 included 10 SHR rats who received PBS vehicle (SHR-V); group 3 included 10 WKY rats who received PBS vehicle (WKY-V). All rats were housed in the animal facility under identical conditions, with a 12 hour light-dark cycle.

Systolic Blood Pressure Measurements

Systolic blood pressure was measured using the non-invasive tail-cuff method (Letica Scientific Instruments LE 5001). Blood pressure values were recorded while the animals were under inhaled anaesthesia (2% isoflurane). The mean of three consecutive measurements was obtained for each animal at study mid-point (6 weeks) and end of study (12 weeks).

Doppler Echocardiography

Cardiac structure and function was assessed at baseline and at the end of the study (12 weeks) using Echocardiography. During the procedure, the animals were under inhaled anaesthesia (isoflurane 2%) and body temperature was maintained using a heat mat. Echocardiography assessment was performed using a Vevo 770 High-Resolution In Vivo Micro-Imaging System (Visualsonics) with a 10 mHz transducer. M-mode and 2-dimensional (2D) images were obtained in the parasternal long- and short-axis views. The interventricular septal thickness, posterior wall thickness, and LV diameter were measured in systole and diastole at the tips of the papillary muscle. Measurements were taken over three consecutive cardiac cycles and averaged. Left ventricular mass (LVM) was calculated according to Devereux's formula and indexed to tibial length (LVMi). Blinded analysis was performed by two separate independent observers.

Serum Collection and BNP Analysis

Blood was collected at baseline via the tail vein method and at the end of the study (12 weeks) during terminal bleed (abdominal aorta). Serum isolation was achieved using Microvette serum tubes (Sarstedt) with centrifugation at 10,000 rpm for 5 minutes at room temperature. Serum levels of the cardiac stress hormone B-type natriuretic peptide (BNP) was quantified using an ultra-sensitive immunoassay with electrochemiluminescence detection as instructed by the manufacturer (Meso Scale Discovery). The assay sensitivity was 1.5 pg/mL.

Myocardial Rat Tissue Collection and Preparation

On completion of the in vivo rat study, animals were sacrificed (terminal bleed while under inhaled 4% isoflurane anaesthesia), and the heart was removed en-bloc to study the impact of 5-aza on collagen deposition within the myocardium. Two methodological approaches were used to quantify collagen deposition, namely, immunostaining of cardiac tissue sections using picrosirus red, and the hydroxyproline assay using tissue lysates.

For picrosirius red staining, the left ventricular midsections (papillary level) of the heart were dissected immediately following sacrifice, rinsed in PBS, and fixed with 10% formalin (Sigma). Formalin fixed tissue was embedded in paraffin and 5 μm thick tissue sections were created for collagen analysis using picrosirius red.

For hydroxyproline quantification, the left ventricular base of the heart was dissected immediately following sacrifice, rinsed in PBS, and snap frozen in liquid nitrogen until required for analysis. Frozen hearts were thawed on ice and individually disrupted and homogenized using an Ultra Turrax T25 Dispersing Instrument (IKA). Total protein within the tissue lystates were quantified using the BCA method and 10 μg of homogenate was used to determine hydroxyproline content. Cardiac tissue was homogenised in PBS at a ratio of 100 mg tissue to 1 ml PBS.

Picrosirius Red Staining and Automated Digital Quantification

Tissue sections were deparaffinised and rehydrated prior to incubating with 0.2% phosphomolibid acid (PMA) for 2 minutes. After rinsing in distilled water, the slides were stained with picrosirius red (Direct Red 80 dissolved in picric acid, Sigma) for 90 minutes. Finally, the slides were placed in 0.4% hydrochloric acid (HCl) for 2 minutes, 70% ethanol for 45 seconds, dehydrated and coverslipped for analysis.

The degree of collagen deposition was quantified by automated digital image analysis. The Aperio ScanScope XT Slide Scanner (Aperio Technologies) system was used to capture whole slide digital images with a 20× objective. Automated image analysis was performed using Imagescope (Aperio). A positive pixel count algorithm was used to automatically quantify the area occupied by the dark pink stain colours representing collagen within each scanned slide image. Calibration of individual staining patterns was performed by specifying the requisite colour (range of hues and saturation) and limits for the desired intensity range. Required input parameters for each stain were based on the HSI (Hue, Saturation and Intensity) colour model. To detect the dark pink colour of collagen with picrosirus red, a hue value of 0.8 was specified. The hue width value of 0.5 was used to allow inclusion of a moderate range of colour shades. A collagen volume fraction was calculated based on the percent of dark pink collagen staining quantified within a tissue section.

Hydroxyproline Assay

In brief, 500 μl of homogenised cardiac tissue sample (ratio of 100 mg tissue homogenised in 1 ml PBS) was incubated at 37° C. in a vacuum oven overnight in 1 ml 6N HCl. Five microlitres of citrate/acetate buffer (7.24% sodium acetate, 5% citric acid, 3.4% sodium hydroxide, 1.2% glacial acetic acid, pH 6.0) and 100 μl chloramine T-solution (282 mg chloramine T, 2 ml n-propanol, 2 ml $H_2O$, 16 ml citrate/acetate buffer) were added to 5 μl of the digested cardiac tissue sample, and incubated for 20 minutes at room temperature. Following incubation, 100 μl of Ehrlich's solution (2.5 g 4-[dimethylamino] benzaldehyde [4-DMAB], 9.3 ml N-propanol, 3.9 ml 70% perchloric acid) was added to each sample and incubated for 20 minutes at 65° C. Samples were subsequently cooled for 10 minutes and read at 550 nm using a SpectraMax M2 plate reader (Molecular Devices) with SoftMax Pro software (Molecular Devices, version 4.7.1). In parallel, a hydroxyproline standard curve was created to generate quantifiable data. Hydroxyproline (Sigma) concentrations from 0-200 μg/ml were used and were handled in a similar fashion to the digested homogenised cardiac tissue samples.

Results

Echocardiography Data

Effect of 5-Aza on Left Ventricular Hypertrophy and Diastolic Dysfunction

As seen from FIGS. 8-11, Echocardiographic analysis revealed a significant reduction in interventricular septum diameter in diastole and left ventricular mass index (LVMI) in the SHR-5AZA group compared to the SHR-V group. The WKY-V control group had significantly less LVH than both SHR groups. Ejection fraction was significantly lower in the SHR-V group compared to the WKY-V group. Treatment with 5AZA significantly increased ejection fraction in SHR animals. E prime (E'), a robust and established echocardiographic measure of diastolic dysfunction, was significantly reduced in SHR-V compared to normotensive WKY-V control. Importantly, this echocardiographic marker of diastolic dysfunction was significantly approved with treatment of 5AZA, equivalent to that of the normotenslve WVKY-V control.

Cardiac Tissue Analysis:

Effect of 5AZA on Myocardial Interstitial Disease

Figure 12:
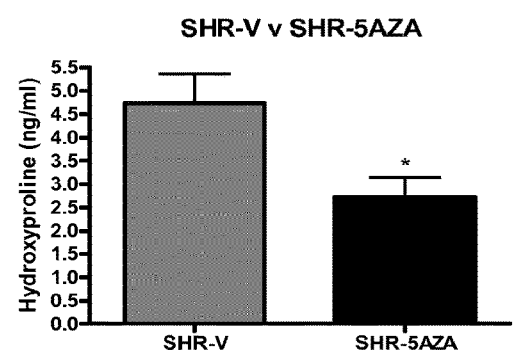
FIG. 12 depicts the effect of 5AZA treatment on collagen content within the heart. Hydroxyproline analysis was carried out to assess total collagen within the myocardium of SHR-V and SHR-5AZA animals. A significant reduction in collagen deposition was detected in SHR-5AZA animals. Results represent mean and standard error of the mean. * $p<0.05$.
Figure 10:
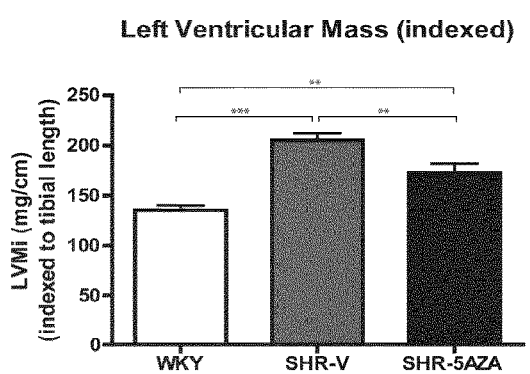

Total collagen content within the myocardium was estimated using the hydroxyproline assay. As highlighted in FIG. 12, a significant reduction in total collagen was observed in SHR rats treated with 5AZA compared to SHR vehicle controls.

Figure 13:
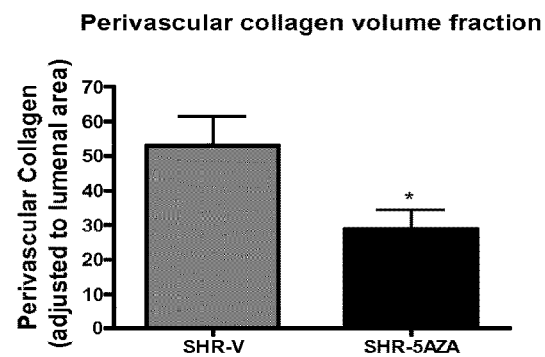
FIGS. 13-15 depict the effect of 5AZA treatment on perivascular collagen. Digital analysis of the slides revealed a significant decrease in perivascular collagen in SHR-5AZA compared to SHR-V. Representative images of picrosirius red stained tissue from one animal is shown. Collagen staining appears pink/red in colour. A mark-up image is generated following digital quantification of positive pixels, highlighting negative pixels as blue and positive pixels as either yellow, orange or red. Results represent mean and standard error of the mean. * $p<0.05$.
Figure 14:
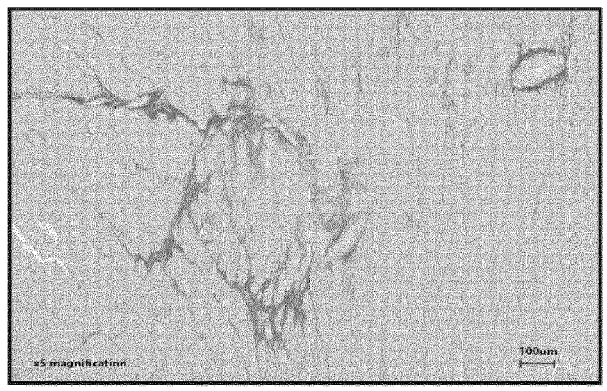
Figure 15:
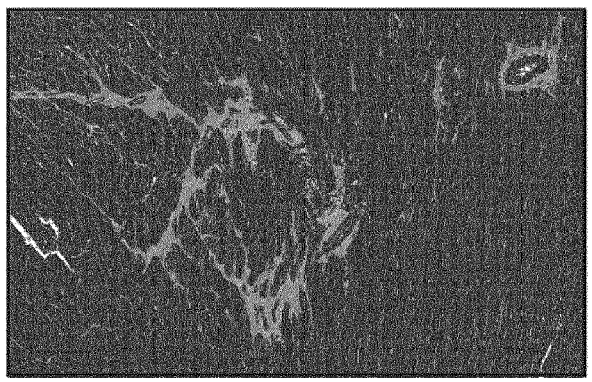

As an indication of collagen distribution and localisation, tissue sections were stained using picrosirius red. The degree of collagen deposition (area occupied by the dark pink stain colours) was quantified by automated digital image analysis through the application of a modified positive pixel count algorithm. Application of the algorithm generated a mark-up image highlighting positive pixels as yellow, orange or red, and negative pixels as blue. A collagen volume fraction was calculated based on the percent of dark pink collagen staining quantified within a tissue section. Results highlight that perivascular collagen was significantly reduced in SHR-5AZA animals compared to SHR-V animals (FIGS. 13-15).

Effect of 5AZA on Cardiac Myocytes In Vivo

Figure 16:
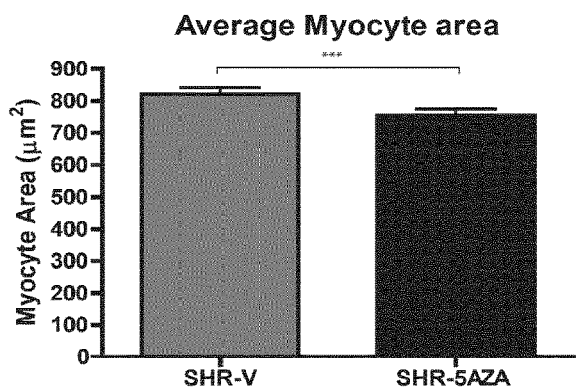
FIG. 16 depicts the effect of 5AZA treatment on myocyte area in vivo. Myocyte area digital analysis of cardiac tissue sections stained with haematoxylin and eosin revealed a significant decrease in cell area in SHR animals treated with 5AZA compared to control animals SHR-V. Results represent mean and standard error of the mean. *** $p<0.001$

Within the cardiac tissue, myocyte area was quantified to assess the ability of 5AZA to reduce myocyte hypertrophy. In this regard, FIG. 16 highlights that the average myocyte area within the SHR-5AZA animals are significantly smaller than that of their counterpart controls SHR-V.

Figure 17:
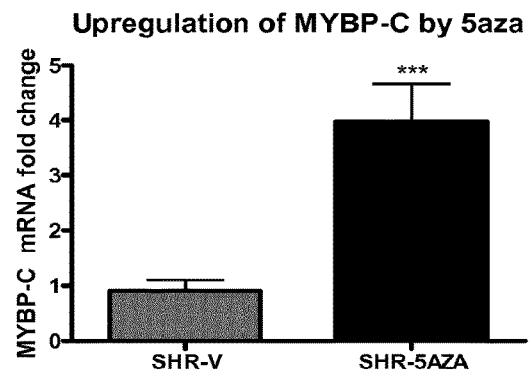
FIGS. 17 and 18 depict the effect of 5AZA treatment on cardiac expression levels of MYBP-C and ACTA1. Gene expression levels of MYBP-C and ACTA1 were assessed using quantitative real-time PCR in the cardiac tissue of SHR-V and SHR-AZA. Analysis reveals that treatment of SHR animals with 5AZA resulted in a significant 4-fold increase in MYBP-C and ACTA1. Results represent mean and standard error of the mean. * $p<0.05$, *** $p<0.001$.

A potential mechanism by which 5AZA improves cardiac function, including hypertrophy and diastology, is through up-regulation of cardiac myosin binding protein C (MYBP-C). It has previously been shown that decreased expression of MYBP-C in the heart results in abnormal contractile function at the myofilament level, thereby contributing to the development of hypertrophic cardiomyopathy in humans. This reduction may be linked with gene mutations as well as through other potential mechanisms. One mechanism yet to be explored is epigenetic changes, including DNA methylation. Re-expressing or increasing the expression levels of MYBP-C through gene transfer in vivo has recently been shown to improve both systolic and diastolic contractile function as well as reduce left ventricular wall thickness (Merkulov et al 2012 Circ HF; PMID:22855556). Our novel data has shown that administration of the demethylating agent 5AZA to an in vivo murine model of hypertensive heart disease resulted in a significant increase in MYBP-C expression within the myocardium (FIG. 17). This highlights a novel mechanism by which MYBP-C expression can be enhanced, and thus has the potential to improve cardiac dysfunction. Treatment with DNA methylation inhibitors, such as 5-azacytidine and 5-aza-2-deoxycytidine could also impact the phosphorylation status of MYBP-C.

Figure 18:
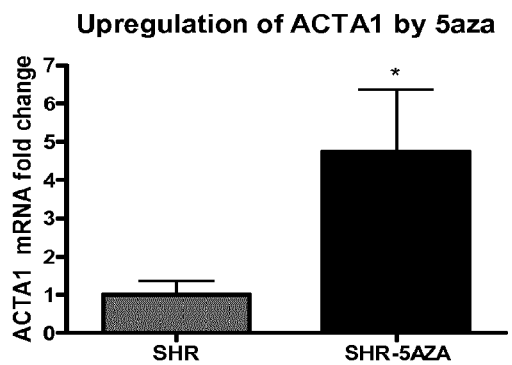
Figure 21:
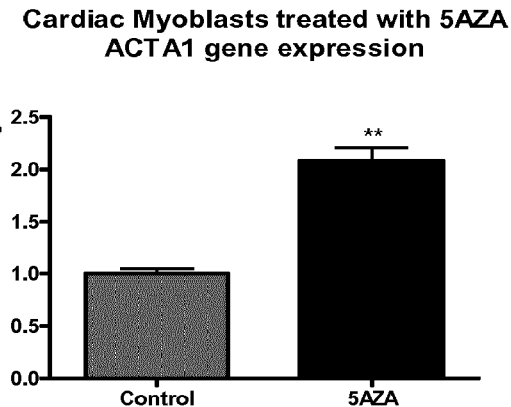
FIGS. 19-22 depict the effect of 5AZA and 5AZA_DC treatment on cardiac myoblast expression levels of MYBP-C and ACTA1 in vitro. Gene expression levels of MYBP-C and ACTA1 were assessed using quantitative real-time PCR following 4 day treatment with DNA demethylating agents 5AZA and 5AZA_DC. Analysis reveals that treatment with these compounds resulted in a significant increase in both MYBP-C and ACTA1 when using either of the two DNA methylation inhibitors. Results represent mean and standard error of the mean. * $p<0.05$,  $p<0.01$, * $p<0.001$.
Figure 19:
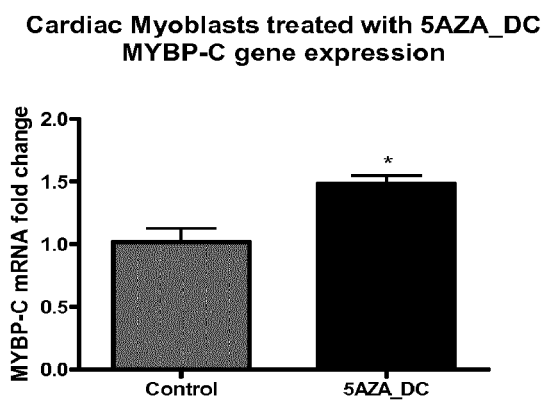
Figure 22:
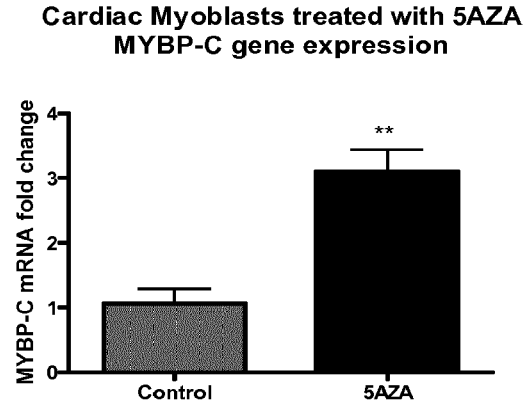
Figure 20:
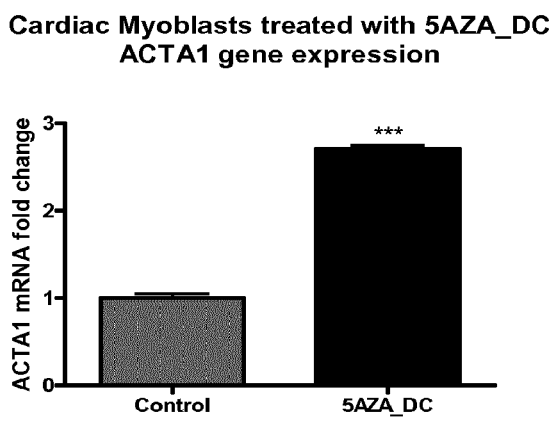

In addition to an increase in MYBP-C gene expression, 5AZA treatment of SHR animals surprisingly resulted in a significant increase in Actin, Alpha 1, Skeletal Muscle (ACTA1), FIG. 18. Up-regulation of MYBP-C and ACTA1 expression were associated with a reduction in hypertrophy and diastolic dysfunction, as indicated by LVMi, E prime, and inter ventricular septum diameter changes.

Cardiac Myoblast Data:

Confirmation of the impact of DNA methylation inhibitors can up-regulate the expression levels of MYBP-C and ACTA1 was assessed in vitro using cardiac myoblast cells. Cells were grown in culture for 4 days either in the presence or absence of 5-azacytidine (5AZA) or 5-aza-2-deoxycytidine (5AZA_DC). Gene expression was quantified using real-time PCR. Treatment with 5AZA_DC resulted in a significant increase in both MYBP-C and ACTA1, as indicated in FIGS. 19-22.

The present invention illustrates the possible utility of hypomethylating agents such as 5-aza and 2'deoxy in the prevention or treatment of cardiomyopathies. In particular, such agents have shown potential for use in treating HCM and myocardial fibrosis. This is particularly surprising, because 5-aza and 2'deoxy have been shown to increase expression of ACTA1, elevated levels of which are implicated in exacerbated hypertrophy. In spite of this, the current data show that these agents nevertheless are capable of reversing the effects of hypertrophy and also the pro-fibrotic impact of hypoxia.

The term "oligonucleotide" is meant to include both standard and modified oligoribonucleotides, oligodeoxyribonucleotides and analogs or combinations thereof. Examples are standard and modified DNA, RNA, and combinations thereof.

The term "or" is intended to be used as listing a number of non-mutually exclusive alternatives. As such, the term "or" should be interpreted to mean "and/or". For example, a statement that an aspect of the invention comprises a method for treating cardiac hypertrophy or myocardial fibrosis, is to be understood as meaning a method for treating any one taken from the set of: cardiac hypertrophy alone; myocardial fibrosis alone; and both cardiac hypertrophy and myocardial fibrosis together.

The words "comprises/comprising" and the words "having/including" when used herein with reference to the present invention are used to specify the presence of stated features, integers, steps or components but do not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The invention claimed is:

1. A method of treating a cardiomyopathy selected from the group consisting of hypertrophic cardiomyopathy, restrictive cardiomyopathy, arrhythmogenic right ventricular cardiomyopathy and endomyocardial fibrosis comprising the step of administering to a patient in need thereof a hypomethylating agent, wherein the hypomethylating agent comprises 5-Azacytidine or 5-Aza-2'-Deoxycytidine, or a pharmaceutically acceptable salt of each thereof.

2. The method of claim 1, wherein the cardiomyopathy is ischemic or non-ischemic cardiomyopathy.

3. The method of claim 1, wherein the cardiomyopathy is hypertrophic cardiomyopathy.

4. The method of claim 1, wherein the treatment of cardiomyopathy is independent of hypertension.

5. The method of claim 1, wherein the hypomethylating agent has the effect of inhibiting the expression or action of DNA methyltransferase1, DNA methyltransferase3A, or DNA methyltransferase3B.

6. A method of preventing a cardiomyopathy selected from the group consisting of hypertrophic cardiomyopathy, restrictive cardiomyopathy, arrhythmogenic right ventricular cardiomyopathy and endomyocardial fibrosis comprising the step of administering to a patient in need thereof a pharmaceutical composition comprising a hypomethylating agent and a pharmaceutically acceptable excipient, wherein the hypomethylating agent comprises 5-Azacytidine or 5-Aza-2'-Deoxycytidine, or a pharmaceutically acceptable salt of each thereof, with the proviso that the patient is not suffering from a cancer or a haematological disease.

7. The method of claim 6, wherein the cardiomyopathy is ischemic or non-ischemic cardiomyopathy.

8. The method of claim 6, wherein the cardiomyopathy is hypertrophic cardiomyopathy.

9. The method of claim 6, wherein the prevention of the cardiomyopathy is independent of hypertension.

10. The method of claim 6, wherein the hypomethylating agent has the effect of inhibiting the expression or action of DNA methyltransferase1, DNA methyltransferase3A, or DNA methyltransferase3B.

11. A method of treating or preventing the development of cardiac hypertrophy or myocardial fibrosis or treating cardiac hypertrophy or myocardial fibrosis comprising the step of administering to a patient in need thereof an agent capable of reducing the expression of, silencing or degrading hypoxia-inducible factor (HIF) protein or HIF mRNA, or an agent capable of preventing HIF protein from binding to hypoxia responsive elements within the promoter regions of DNA methyltransferase genes, wherein the agent is an oligonucleotide of sequence SEQ ID 31 or a pharmaceutically acceptable salt thereof.

12. A method of preventing the establishment of new methylation onto newly synthesized DNA thereby treating a cardiomyopathy selected from the group of: hypertrophic cardiomyopathy, restrictive cardiomyopathy, arrhythmogenic right ventricular cardiomyopathy or endomyocardial fibrosis, in patient in need thereof comprising administering to the patient an agent that comprises 5-Azacytidine or 5-Aza-2'-Deoxycytidine or a pharmaceutically acceptable salt of each thereof.

13. The method of claim 12, wherein the cardiomyopathy is ischemic or non-ischemic cardiomyopathy.

14. The method of claim 12, wherein the cardiomyopathy is hypertrophic cardiomyopathy.

15. The method of claim 1, wherein the method is for preventing the development of a cardiomyopathy.

16. The method of claim 6, wherein the method is for the development of a cardiomyopathy.

* * * * *